US008492519B2

(12) United States Patent
Grallert et al.

(10) Patent No.: US 8,492,519 B2
(45) Date of Patent: Jul. 23, 2013

(54) PROTEASE-STABLE, CELL WALL-LYSING ENZYMES

(75) Inventors: Holger Grallert, Weilheim (DE); Michael Forchheim, Regensburg (DE)

(73) Assignees: Hyglos Invest GmbH, Bernried (DE); bioMérieux S.A., Marcy l'Etoile (FR)

( * ) Notice: Subject to any disclaimer, the term of this patent is extended or adjusted under 35 U.S.C. 154(b) by 455 days.

(21) Appl. No.: 12/674,369

(22) PCT Filed: Aug. 19, 2008

(86) PCT No.: PCT/DE2008/001378
§ 371 (c)(1),
(2), (4) Date: May 4, 2010

(87) PCT Pub. No.: WO2009/024142
PCT Pub. Date: Feb. 26, 2009

(65) Prior Publication Data
US 2010/0216711 A1    Aug. 26, 2010

Related U.S. Application Data

(60) Provisional application No. 60/957,351, filed on Aug. 22, 2007, provisional application No. 61/032,211, filed on Feb. 28, 2008.

(30) Foreign Application Priority Data

Aug. 22, 2007  (EP) ..................................... 07114785
Dec. 21, 2007  (DE) ......................... 10 2007 061 929
Feb. 28, 2008  (EP) ..................................... 08152096
May 14, 2008  (DE) ......................... 10 2008 023 448

(51) Int. Cl.
*C07K 1/00* (2006.01)
(52) U.S. Cl.
USPC ................. 530/350; 424/234.1; 424/239.1; 424/246.1; 424/243.1; 424/244.1; 424/248.1
(58) Field of Classification Search
None
See application file for complete search history.

(56) References Cited

U.S. PATENT DOCUMENTS 6,432,444 B1   8/2002   Fischetti et al. .............. 424/443

FOREIGN PATENT DOCUMENTS

EP       A-1 862 080       12/2007

OTHER PUBLICATIONS

Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Copeland et al., "SH3, type-5 domain protein", Database accession No. A5IUB2__STAA9, 2007.
Croux et al., "Interchange of functional domains switches enzyme specificity: Construction of a chimeric phneumococcal-clostridial cell wall lytic enzyme" *Molecular Microbiology*, Blackwell Scientific, Oxford, GB vol. 9, No. 5, 1993, pp. 1019-1025.
Diaz et al., "Chimeric phage-bacterial enzymes a clue to the modualr evolution of genes" *Proceedings of the National Acaddmy of sciences of the United State of America*, vol. 87, No. 20, 1990, pp. 8125-8129.
Donovan, "Peptidoglycan hydrolase fusions maintain their parental specificities" *Applied and Environmental Microbiology*, vol. 72, No. 4, Apr. 2006, pp. 2988-2996.
Iandolo et al., "Amidase", Database accession No. Q8SDS7__BP-PHA, 2002.
Kuroda et al., "Truncated amidase", Database accession No. Q931m6__STAA9, 2007.
Matisizaki et al., "*Staphylococcus aureaus* related bacteriphage protein #7", Database accession No. AND01958, 2004.
Matsuzaki et al., "*Staphylococcus aureaus* related bacteriophage protein #3", Database accession No. ADN1954, 2004.
Rawlings et al., "MEROPS: The peptidase database", *Nucleic Acids Res* 36, D320-325, 2008.
Sao-Jose et al., "The N-terminal region of the *Oenococcus oeni* bacteriophage fog44 lysin behaves as a bona fide signal peptide in *Escherichia coli* and as a cis-inhibitory element, preventing lytic activity on oenococcal cells" *Journal of Bacteriology* vol. 182, No. 20, Oct. 2000, pp. 5823-5831.

* cited by examiner

*Primary Examiner* — Jennifer Graser
(74) *Attorney, Agent, or Firm* — Parker Highlander PLLC

(57) ABSTRACT

The present invention relates to a modified polypeptide with a biological activity to lyse cell walls of bacteria, wherein the polypeptide has no caspase, clostripain, enterokinase, factor Xa, granzyme B, *staphylococcus* peptidase I (V8 Protease), plasmin, streptopain, bacillolysin and/or thrombin cleavage site. The invention further relates to nucleic acids with a sequence encoding a polypeptide according to the present invention.

4 Claims, 12 Drawing Sheets

Fig. 1

```
          10         20         30         40         50         60
MSIIMEVATM QAKLTKKEFI EWLKTSEGKQ FNVDLWYGFQ CFDYANAGWK VLFGLLLKGL 70         80         90        100        110        120
GAKDIPFANN FDGLATVYQN TPDFLAQPGD MVVFGSNYGA GYGHVAWVIE ATLDYIIVYE 130        140        150        160        170        180
QNWLGGGWTD RIEQPGWGWE KVTRRQHAYD FPMWFIRPNF KSETAPRSIQ SPTQASKKET 190        200        210        220        230        240
AKPQPKAVEL KIIKDVVKGY DLPKRGGNPK GIVIHNDAGS KGATAEAYRN GLVNAPSSRL 250        260        270        280        290        300
EAGIAHSYVS GNTVWQALDE SQVGWHTANQ LGNKYYYGIE VCQSMGADNA TFLKNEQATF 310        320        330        340        350        360
QECARLLKKW GLPANRNTIR LHNEFTSTSC PHRSSVLHTG FDPVTRGLLP EDKRLQLKDY 370        380        390
FIKQIRAYMD GKIPVATVSN ESSASSNTVK PVA
```

Fig. 2
A
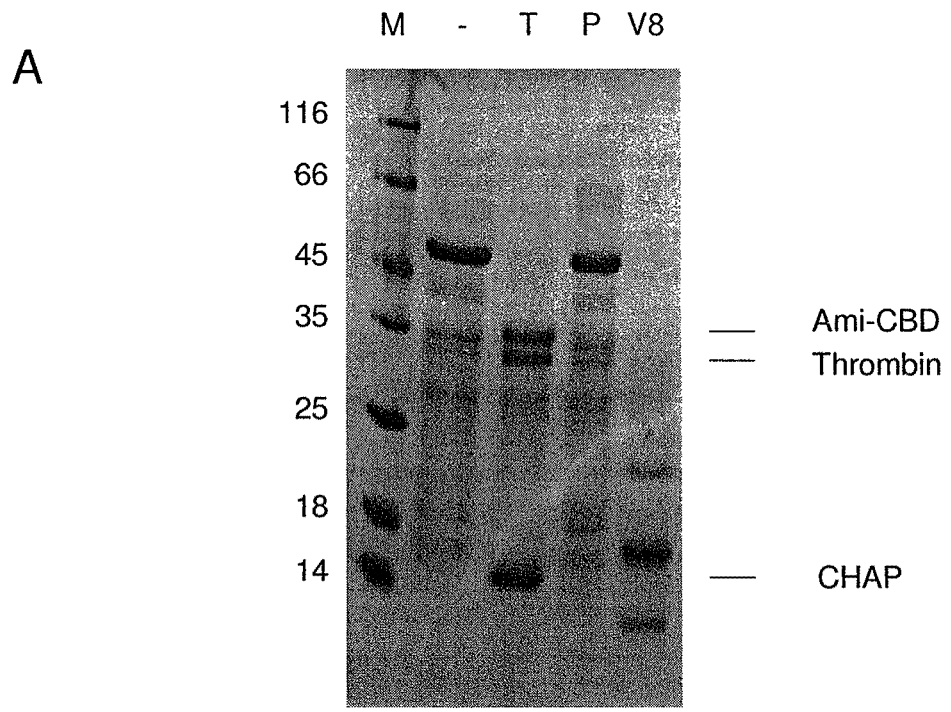
B
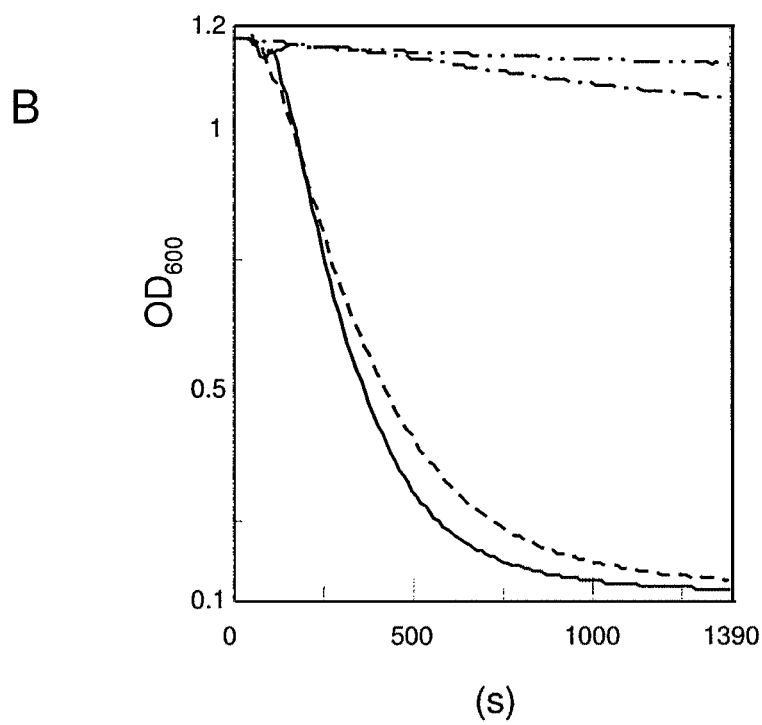

Fig. 3
A
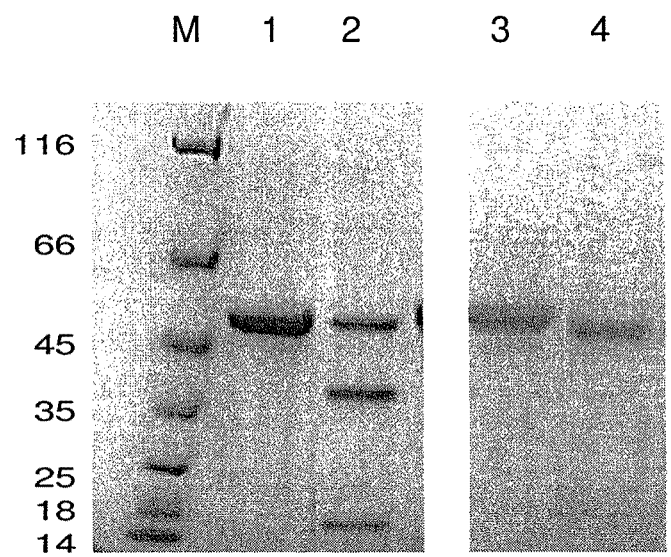
B
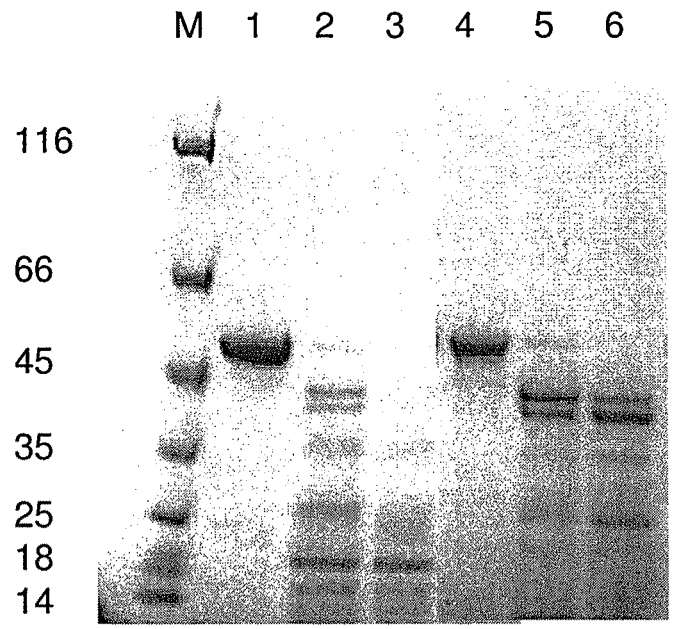

Fig. 4

```
CD119    MKIGVNCGHTKTGAGSGAIGKINESIETRNVGYKVIDKLKTLGNNVVDCTIDKASTQSEC  60
630      MKIGINCGHTKTGAGSGAIGKINESIETRNVGYKVIDKLKKLGNNVVDCTIDKASTQSEC  60
         ****:*******************************:***********************
                                              Thrombin
CD119    LSKIATQANRQDLDWFISIHFNAGKGRGCEVYTYKGKQYQDAIDVCKKISDLGFTNRGVK 120
630      LSKITAQANRQDLDWFISIHFNAGGGKGCEVYTYKGKQYQDAIDVCKKISDLGFTNRGVK 120
         ****::******************  *:********************************

CD119    DGSGLYVVKKTKAKSMLIEVCFVDSEDANKYLSLGADKLATAIVEAITKHISSAEENNYN 180
630      DGSGLYVVKKTKAKSMLIEVCFVDTEDANKYLSLGADKLATAIVEAITKHISSAEENNYN 180
         ************************:***********************************
                                                    Caspase 1
CD119    RYKHTIVYSGDDKVSADILGLYYKRKKESYVTDIKDYKPHRTQNLYVIGGVTCNKMKEM  240
630      RYKHTIVYSGDDKVSADILGLYYKRKKESYLVTDIKDYKPHRTQNLYVIGGVTCNKMKEM 240
         *********************************************************

CD119    SKTTGEKFTQLYGNDVWSTMDKAIEFVKEKL 271
630      SKTTGEKFTQLYGNDVWSTMDKAIEFVKEKL 271
         ******************************
```

Fig. 5

```
15     QNWLGGGWTDGIEQPAGVGKKLQDDNMLMISLCGLSVRILK-VRQRHDQFNLLHKHPKKE 170
16     QNWLGGGWTDGIEQPAGVGKKLQDDNMLMISLCGLSVRILK-VRQRHDQFNLLHKHPKKE 170
3      QNWLGGGWTDRIEQPGWGWEKVTRRQHAYDFPMWFIRPNFK-SETAPRSIQSPTQASKKE 170
4      QNWLGGGWTDRIEQPGWGWEKVTRRQHAYDFPMWFIRPNFK-SETAPRSIQSPTQASKKE 170
5      QNWLGGGWTDRIEQPGWGWEKVTRRQHAYDFPMWFIRPNFK-SETAPRSIQSPTQASKKE 170
P26A   QNWLGGGWTDRIEQPGWGWEKVTRRQHAYDFPMWFIRPNFK-SETAPRSIQSPTQASKKE 179
9      QNWLGGGWTDGIEQPGWGWEKVTRRQHAYDFPMWFIRPNFK-SETAPRSVQSPTQAPKKE 170
10     QNWLGGGWTDGIEQPGWGWEKVTRRQHAYDFPMWFIRPNFK-SEIAPRSVQSPTQAPKKE 170
11     QNWLGGGWTDGIEQPGWGWEKVTRRQHAYDFPMWFIRPNFK-SEITPRSVQSPTQAPKKE 170
12     QNWLGGGWTDGIEQPGWGWEKVTRRQHAYDFPMWFIRPNFK-SETAPRSVQSPTQAPKKE 170
13     QNWLGGGWTDGIEQPGWGWEKVTRRKHAYDFPMWFIRPNFK-SEIAPRSVQSPTQAPKKE 170
14     QNWLGGGWTDGIEQPGWGWEKVTRRQHAYDFPMWFIRPNFK-SEIAPRSVQSPTQAPKKE 170
2      QNWLGGGWTDGIEQPGWGWEKVTRRQHAYDFPMWFIRPNFK-SETAPRSVQSPTQAPKKE 179
8      QNWLGGGWTDGIEQPGWGWEKVTRRQHAYDFPMWFIRPNFK-SETAPRSVQSPTQAPKKE 170
7      QNWLGGGWTDGIEQPGWGWEKVTRRQHAYDFPMWFIRPNFK-SETAPRSVQSPTQAPKKE 170
1      QNWLGGGWTDGIEQPGWGWEKVTRRQHAYDFPMWFIRPNFK-SETAPRSVQSPTQAPKKE 170
6      QNWLGGGWTDGVQQPGSGWEKVTRRQHAYDFPMWFIRPNFK-SETAPRSVQSPTQASKKE 170
17     QNWLGGGWTDGIEQPGWGWEKVTRRQHAYDFPMFFIRPKFK-TATATRSAQSPTQSVKKA 170
18     QNWLGGGWTNGPEQGGTGWEKATRRTHGYDFPMWFIRPNFKQTDVTVKSSQSATVGDKKS 171
       *********.:*  . :*         :    :*     .  :       **
```

Fig. 6/1

(A) CHAP-Ami_Pitti26-CBD_USA

```
MSIIMEVATM QAKLTKKEFI EWLKTSEGKQ FNVDLWYGFQ CFDYANAGWK VLFGLLLKGL    60
GAKDIPFANN FDGLATVYQN TPDFLAQPGD MVVFGSNYGA GYGHVAWWIE ATLDYIIVYE   120
QNWLGGGWTD RIEQPGWGWE KVTRRQHAYD FPMWFIRPNF KSETAPRSIQ SPTQASKKET   180
AKPQPKAVEL KIIKDVVKGY DLPKRGGNPK GIVIHNDAGS KGATAEAYRN GLVNAPSSRL   240
EAGIAHSYVS GNTVWQALDE SQVGWHTANQ LGNKYYYGIE VCQSMGADNA TFLKNEQATF   300
QECARLLKKW GLPANRNTIR LHNEFTSTSC PHRSSVLHTG FDPVTRGLLP EDKRLQLKDY   360
FIKQIRAYMD GKIPVATVSN ESSASSNTVK PVAELMPPVP AGYTLDKNNV PYKKEQGNYT   420
VANVKGNNVR DGYSTNSRIT GVLPNNTTIT YDGAYCINGY RWITYIANSG QRRYIATGEV   480
DIAGNRISSF GKFSAV
```

(B) CHAP-Ami_Pitti26-CBD_USA mutant 4, table 3

```
MSIIMEVATM QAKLTKKEFI EWLKTSEGKQ FNVDLWYGFQ CFDYANAGWK VLFGLLLKGL    60
GAKDIPFANN FDGLATVYQN TPDFLAQPGD MVVFGSNYGA GYGHVAWWIE ATLDYIIVYE   120
QNWLGGGWTD RIEQPGWGWE KVTRRQHAYD FPMWFIRPNF KSATAPASIQ SPTQASKKET   180
AKPQPKAVEL KIIKDVVKGY DLPKRGGNPK GIVIHNDAGS KGATAEAYRN GLVNAPSSRL   240
EAGIAHSYVS GNTVWQALDE SQVGWHTANQ LGNKYYYGIE VCQSMGADNA TFLKNEQATF   300
QECARLLKKW GLPANRNTIR LHNEFTSTSC PHRSSVLHTG FDPVTRGLLP EDKRLQLKDY   360
FIKQIRAYMD GKIPVATVSN ESSASSNTVK PVAELMPPVP AGYTLDKNNV PYKKEQGNYT   420
VANVKGNNVR DGYSTNSRIT GVLPNNTTIT YDGAYCINGY RWITYIANSG QRRYIATGEV   480
DIAGNRISSF GKFSAV
```

(C) CHAP-Ami_Pitti26-CBD_USA mutant 10, table 3

```
MSIIMEVATM QAKLTKKEFI EWLKTSEGKQ FNVDLWYGFQ CFDYANAGWK VLFGLLLKGL    60
GAKDIPFANN FDGLATVYQN TPDFLAQPGD MVVFGSNYGA GYGHVAWWIE ATLDYIIVYE   120
QNWLGGGWTD RIEQPGWGWE KVTRRQHAYD FPMWFIRPNF KSQTAPASIQ SPTQASKKAT   180
AKPQPKAVQL KIIKDVVKGY DLPKRGGNPK GIVIHNDAGS KGATAEAYRN GLVNAPSSRL   240
EAGIAHSYVS GNTVWQALDE SQVGWHTANQ LGNKYYYGIE VCQSMGADNA TFLKNEQATF   300
QECARLLKKW GLPANRNTIR LHNEFTSTSC PHRSSVLHTG FDPVTRGLLP EDKRLQLKDY   360
FIKQIRAYMD GKIPVATVSN ESSASSNTVK PVAELMPPVP AGYTLDKNNV PYKKEQGNYT   420
VANVKGNNVR DGYSTNSRIT GVLPNNTTIT YDGAYCINGY RWITYIANSG QRRYIATGEV   480
DIAGNRISSF GKFSAV
```

(D) CHAP-Ami_Pitti26-CBD_USA mutant 13, table 3

```
MSIIMEVATM QAKLTKKEFI EWLKTSEGKQ FNVDLWYGFQ CFDYANAGWK VLFGLLLKGL    60
GAKDIPFANN FDGLATVYQN TPDFLAQPGD MVVFGSNYGA GYGHVAWWIE ATLDYIIVYE   120
QNWLGGGWTD RIEQPGWGWE KVTRRQHAYD FPMWFIRPNF KSETAPASIQ SPTQASKKET   180
AKPQPKAVEL KIIKDVVKGY DLPKRGGNPK GIVIHNDAGS KGATAEAYRN GLVNAPSSRL   240
EAGIAHSYVS GNTVWQALDE SQVGWHTANQ LGNKYYYGIE VCQSMGADNA TFLKNEQATF   300
QECARLLKKW GLPANRNTIR LHNEFTSTSC PHRSSVLHTG FDPVTRGLLP EDKRLQLKDY   360
FIKQIRAYMD GKIPVATVSN ESSASSNTVK PVAELMPPVP AGYTLDKNNV PYKKEQGNYT   420
VANVKGNNVR DGYSTNSRIT GVLPNNTTIT YDGAYCINGY RWITYIANSG QRRYIATGEV   480
DIAGNRISSF GKFSAV
```

(E) CHAP-Ami_Pitti26-CBD_USA mutant 2, table 3

```
MSIIMEVATM QAKLTKKEFI EWLKTSEGKQ FNVDLWYGFQ CFDYANAGWK VLFGLLLKGL    60
GAKDIPFANN FDGLATVYQN TPDFLAQPGD MVVFGSNYGA GYGHVAWWIE ATLDYIIVYE   120
QNWLGGGWTD RIEQPGWGWE KVTRRQHAYD FPMWFIRPNF KSQTAPASIQ SPTQASKKET   180
AKPQPKAVEL KIIKDVVKGY DLPKRGGNPK GIVIHNDAGS KGATAEAYRN GLVNAPSSRL   240
EAGIAHSYVS GNTVWQALDE SQVGWHTANQ LGNKYYYGIE VCQSMGADNA TFLKNEQATF   300
QECARLLKKW GLPANRNTIR LHNEFTSTSC PHRSSVLHTG FDPVTRGLLP EDKRLQLKDY   360
FIKQIRAYMD GKIPVATVSN ESSASSNTVK PVAELMPPVP AGYTLDKNNV PYKKEQGNYT   420
VANVKGNNVR DGYSTNSRIT GVLPNNTTIT YDGAYCINGY RWITYIANSG QRRYIATGEV   480
DIAGNRISSF GKFSAV
```

Fig. 6/2

(F) CHAP-Ami_Pitti26-CBD_USA-Add2

```
MASIIMEVAT MQAKLTKKEF IEWLKTSEGK QFNVDLWYGF QCFDYANAGW KVLFGLLLKG    60
LGAKDIPFAN NFDGLATVYQ NTPDFLAQPG DMVVFGSNYG AGYGHVAWVI EATLDYIIVY   120
EQNWLGGGWT DRIEQPGWGW EKVTRRQHAY DFPMWFIRPN FKSETAPRSI QSPTQASKKE   180
TAKPQPKAVE LKIIKDVVKG YDLPKRGGNP KGIVIHNDAG SKGATAEAYR NGLVNAPSSR   240
LEAGIAHSYV SGNTVWQALD ESQVGWHTAN QLGNKYYYGI EVCQSMGADN ATFLKNEQAT   300
FQECARLLKK WGLPANRNTI RLHNEFTSTS CPHRSSVLHT GFDPVTRGLL PEDKRLQLKD   360
YFIKQIRAYM DGKIPVATVS NESSASSNTV KPVAELMPPV PAGYTLDKNN VPYKKEQGNY   420
TVANVKGNNV RDGYSTNSRI TGVLPNNTTI TYDGAYCING YRWITYIANS GQRRYIATGE   480
VDIAGNRISS FGKFSAV                                                  497
```

(G) CHAP-Ami_Pitti26-CBD_USA-Add2 as mutant 4, table 3

```
MASIIMEVAT MQAKLTKKEF IEWLKTSEGK QFNVDLWYGF QCFDYANAGW KVLFGLLLKG    60
LGAKDIPFAN NFDGLATVYQ NTPDFLAQPG DMVVFGSNYG AGYGHVAWVI EATLDYIIVY   120
EQNWLGGGWT DRIEQPGWGW EKVTRRQHAY DFPMWFIRPN FKSATAPASI QSPTQASKKE   180
TAKPQPKAVE LKIIKDVVKG YDLPKRGGNP KGIVIHNDAG SKGATAEAYR NGLVNAPSSR   240
LEAGIAHSYV SGNTVWQALD ESQVGWHTAN QLGNKYYYGI EVCQSMGADN ATFLKNEQAT   300
FQECARLLKK WGLPANRNTI RLHNEFTSTS CPHRSSVLHT GFDPVTRGLL PEDKRLQLKD   360
YFIKQIRAYM DGKIPVATVS NESSASSNTV KPVAELMPPV PAGYTLDKNN VPYKKEQGNY   420
TVANVKGNNV RDGYSTNSRI TGVLPNNTTI TYDGAYCING YRWITYIANS GQRRYIATGE   480
VDIAGNRISS FGKFSAV                                                  497
```

(H) CHAP-Ami_Pitti26-CBD_USA-Add2 as mutant 10, table 3

```
MASIIMEVAT MQAKLTKKEF IEWLKTSEGK QFNVDLWYGF QCFDYANAGW KVLFGLLLKG    60
LGAKDIPFAN NFDGLATVYQ NTPDFLAQPG DMVVFGSNYG AGYGHVAWVI EATLDYIIVY   120
EQNWLGGGWT DRIEQPGWGW EKVTRRQHAY DFPMWFIRPN FKSQTAPASI QSPTQASKKA   180
TAKPQPKAVQ LKIIKDVVKG YDLPKRGGNP KGIVIHNDAG SKGATAEAYR NGLVNAPSSR   240
LEAGIAHSYV SGNTVWQALD ESQVGWHTAN QLGNKYYYGI EVCQSMGADN ATFLKNEQAT   300
FQECARLLKK WGLPANRNTI RLHNEFTSTS CPHRSSVLHT GFDPVTRGLL PEDKRLQLKD   360
YFIKQIRAYM DGKIPVATVS NESSASSNTV KPVAELMPPV PAGYTLDKNN VPYKKEQGNY   420
TVANVKGNNV RDGYSTNSRI TGVLPNNTTI TYDGAYCING YRWITYIANS GQRRYIATGE   480
VDIAGNRISS FGKFSAV                                                  497
```

(I) CHAP-Ami_Pitti26-CBD_USA-Add2 as mutant 13, table 3

```
MASIIMEVAT MQAKLTKKEF IEWLKTSEGK QFNVDLWYGF QCFDYANAGW KVLFGLLLKG    60
LGAKDIPFAN NFDGLATVYQ NTPDFLAQPG DMVVFGSNYG AGYGHVAWVI EATLDYIIVY   120
EQNWLGGGWT DRIEQPGWGW EKVTRRQHAY DFPMWFIRPN FKSETAPASI QSPTQASKKE   180
TAKPQPKAVE LKIIKDVVKG YDLPKRGGNP KGIVIHNDAG SKGATAEAYR NGLVNAPSSR   240
LEAGIAHSYV SGNTVWQALD ESQVGWHTAN QLGNKYYYGI EVCQSMGADN ATFLKNEQAT   300
FQECARLLKK WGLPANRNTI RLHNEFTSTS CPHRSSVLHT GFDPVTRGLL PEDKRLQLKD   360
YFIKQIRAYM DGKIPVATVS NESSASSNTV KPVAELMPPV PAGYTLDKNN VPYKKEQGNY   420
TVANVKGNNV RDGYSTNSRI TGVLPNNTTI TYDGAYCING YRWITYIANS GQRRYIATGE   480
VDIAGNRISS FGKFSAV                                                  497
```

(K) CHAP-Ami_Pitti26-CBD_USA-Add2 as mutant 2, table 3

```
MASIIMEVAT MQAKLTKKEF IEWLKTSEGK QFNVDLWYGF QCFDYANAGW KVLFGLLLKG    60
LGAKDIPFAN NFDGLATVYQ NTPDFLAQPG DMVVFGSNYG AGYGHVAWVI EATLDYIIVY   120
EQNWLGGGWT DRIEQPGWGW EKVTRRQHAY DFPMWFIRPN FKSQTAPASI QSPTQASKKE   180
TAKPQPKAVE LKIIKDVVKG YDLPKRGGNP KGIVIHNDAG SKGATAEAYR NGLVNAPSSR   240
LEAGIAHSYV SGNTVWQALD ESQVGWHTAN QLGNKYYYGI EVCQSMGADN ATFLKNEQAT   300
FQECARLLKK WGLPANRNTI RLHNEFTSTS CPHRSSVLHT GFDPVTRGLL PEDKRLQLKD   360
YFIKQIRAYM DGKIPVATVS NESSASSNTV KPVAELMPPV PAGYTLDKNN VPYKKEQGNY   420
TVANVKGNNV RDGYSTNSRI TGVLPNNTTI TYDGAYCING YRWITYIANS GQRRYIATGE   480
VDIAGNRISS FGKFSAV                                                  497
```

Fig. 7

(A)

```
  1 mkigincght ktgagsgaig kinesietrn vgykvidklk klgnnvvdct idkastqsec
 61 lskitaqanr qdldwfisih fnagggkgce vytykgkqyq daidvckkis dlgftnrgvk
121 dgsglyvvkk tkaksmliev cfvdtedank ylslgadkla taiveaitkh issaeennyn
181 rykhtivysg ddkvsadilg lyykrkkesy lvteikdykp hrtqnlyvig gvtcnkmkem
241 skttgekftq lygndvwstm dkaiefvkek l
```

(B)

```
  1 mkigvncght ktgagsgaig kinesietrn vgykvidklk tlgnnvvdct idkastqsec
 61 lskiatqanr qdldwfisih fnagkgkgce vytykgkqyq daidvckkis dlgftnrgvk
121 dgsglyvvkk tkaksmliev cfvdsedank ylslgadkla taiveaitkh issaeennyn
181 rykhtivysg ddkvsadilg lyykrkkesy lvteikdykp hrtqnlyvig gvtcnkmkem
241 skttgekftq lygndvwstm dkaiefvkek l
```

Fig. 8

MVKYTVENKI IAGLPKGKLK GANFVIAHET ANSKSTIDNE VSYMTRNWKN AFVTHFVGGG
GRVVQVANVN YVSWGAGQYA NSYSYAQVEL CRTSNATTFK KDYEVYCQLL VDLAKKAGIP
ITLDSGSKTS DKGIKSHKWV ADKLGGTTHQ DPYAYLSSWG ISKAQFASDL AKVSGGGNTG
TAPAKPSTPA PKPSTPSTNL DKLGLVDYMN AKKMDSSYSN RDKLAKQYGI ANYSGTASQN
TTLLSKIKGG APKPSTPAPK PSTSTAKKIY FPPNKGNWSV YPTNKAPVKA NAIGAINPTK
FGGLTYTIQK DRGNGVYEIQ TDQFGRVQVY GAPSTGAVIK K

Fig. 9

```
MVKYTVENKI IAGLPKGKLK GANFVIAHET ANSKSTIDNE VSYMTRNWKN AFVTHFVGGG
GRVVQVANVN YVSWGAGQYA NSYSYAQVEL CRTSNATTFK KDYEVYCQLL VDLAKKAGIP
ITLDSGSKTS DKGIKSHKWV ADKLGGTTHQ DPYAYLSSWG ISKAQFASDL AKVSGGGNTG
TAPAKPSTPA PKPSTPSTNL DKLGLVDYMN AKKMDSSYSN RDKLAKQYGI ANYSGTASQN
TTLLSKIKGG APKPSTPAPK PSTSTAKKIY FPPNKGNWSV YPTNKAPVKA NAIGAINPTK
FGGLTYTIQK DRGNGVYEIQ TDQFGRVQVY GAPSTGAVIK K
```

Fig. 10
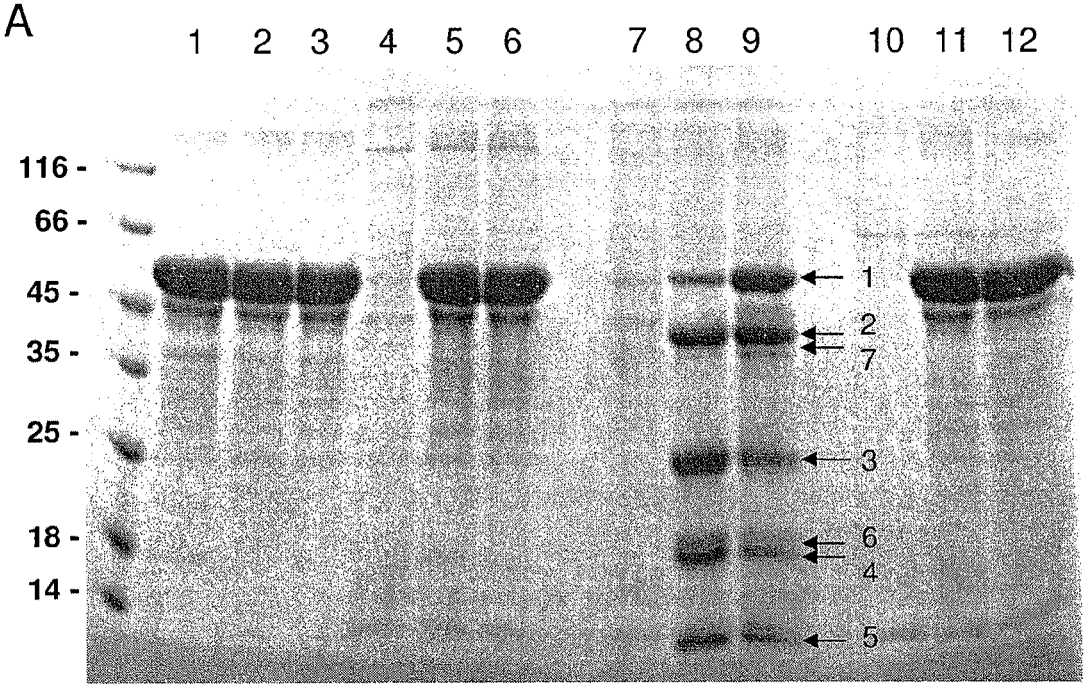
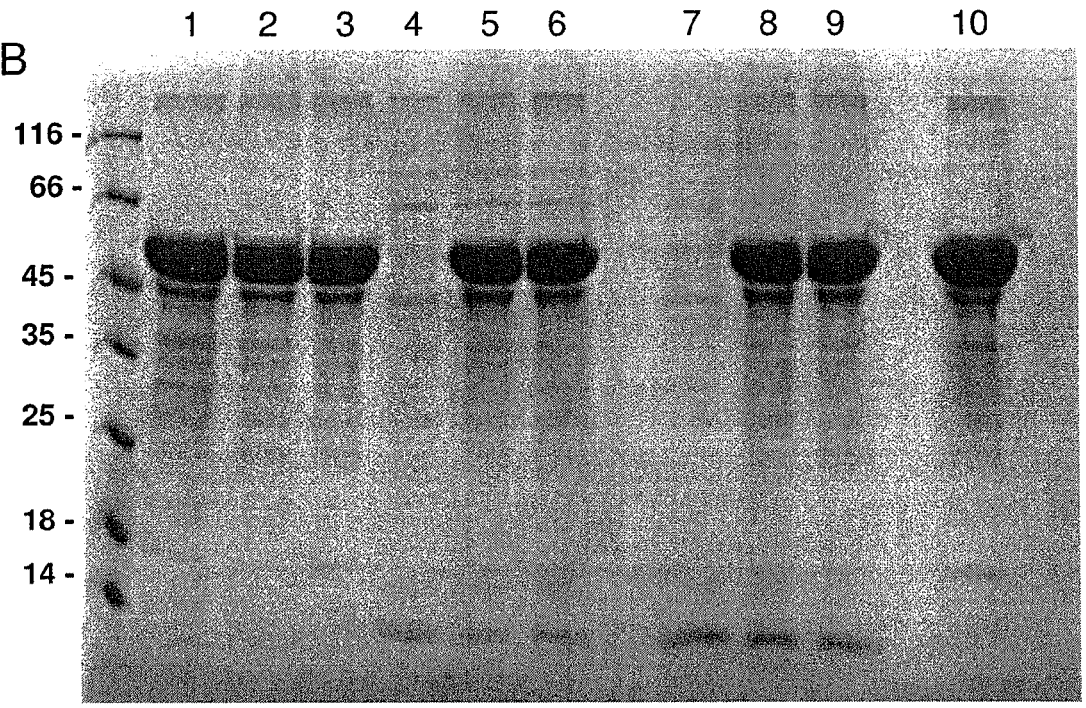

Fig. 11

```
          10         20         30         40         50         60
MASIIMEVAT MQAKLTKKEF IEWLKTSEGK QFNVDLWYGF QCFDYANAGW KVLFGHTLKG 70         80         90        100        110        120
LGAKDIPFAN NFDGLATVYQ NTPDFLAQPG DMVVFGSNYG AGYGHVAWVI EATLDYIIVY 130        140        150        160        170        180
EQNWLGGGWT DRIEQPGWGW EKVTRRQHAY DFPMWFIRPN FKSATAPASI QSPTQASKKE 190        200        210        220        230        240
TAKPQPKAVE LKIIKDVVKG HDLPKRGGNP KGIVIHNDAG SKGATAEAYR NGLVNAPSSR 250        260        270        280        290        300
LEAGIAHSYV SGNTVWQALD ESQVGWHTAN QLGNKYYYGI EVCQSMGADN ATFLKNEQAT 310        320        330        340        350        360
FQECARLLKK WGLPANRNTI RLHNEFTSTS CPHRSSVLHT GFDPVTRGLL PEDKRLQLKD 370        380        390        400        410        420
YFIKQIRAYM DGKIPVATVS NESSASSNTV KPVAELMPPV PAGYTLDKNN VPYKKEQGNY 430        440        450        460        470        480
TVANVKGNNV RDGYSTNSRI TGVLPNNTTI TYDGAYCING YRWITYIANS GQRRYIATGE

490
VDIAGNRISS FGKFSAV
```

Fig. 12

```
                    1                                                           60
Phage SAP-2     MKSQQQAKDWIYKHEGVGVDFDGAYGFQCMDLAVAYIY YITDG KVRMWGNAKDAINNDFK
Phage 44AHJD    MKSQQQAKEWIYKHEGAGVDFDGAYGFQCMDLSVAYVY YITDG KVRMWGNAKDAINNDFK
Phage 66        MKSQQQAKEWIYNHEGAGVDFDGAYGFQCMDLAVAYVY YITDG KVRMWGNAKDAINNDFK
```

PROTEASE-STABLE, CELL WALL-LYSING ENZYMES

This application is a national phase application under 35 U.S.C. §371 of International Patent Application No. PCT/DE 2008/001378 filed Aug. 19, 2008 claims priority to European Patent Application No. EP 07 114 785.4 filed Aug. 22, 2007, U.S. Provisional Patent Application No. 60/957,351 filed Aug. 22, 2007, German Patent Application No. DE 10 2007 061 929.6 filed Dec. 21, 2007, U.S. Provisional Patent Application No. 61/032,211 filed Feb. 28, 2008, European Patent Application No. EP 08 152 096.7 filed Feb. 28, 2008 and German Patent Application No. DE 10 2008 023 448.6 filed May 14, 2008. The entire text of each of the above-referenced disclosures is specifically incorporated herein by reference without disclaimer.

The present invention relates to a modified polypeptide with a biological activity to lyse cell walls of bacteria, wherein the polypeptide has no caspase, clostripain, enterokinase, factor Xa, granzyme B, *staphylococcus* peptidase I (V8 Protease), plasmin, streptopain, bacillolysin and/or thrombin cleavage site. The invention further relates to nucleic acids with a sequence encoding a polypeptide according to the present invention.

Pathogenic bacteria appear at many places and cause enormous health problems by infections as well as high economic costs, e.g. also by unwanted bacteria contamination in the food, cosmetic and environmental industry. In health care the problems are increasing more and more due to germs resistant to antibiotics, so that it is searched hand-wringing for alternatives to antibiotics. In the food and cosmetic industry it is increasingly tried to manage without the classical preservatives, which seek acceptance in the population less and less. As a solution for these problems the use of cell wall lysing enzymes is indicated which prevent naturally the growth of the unexpected bacteria and kill existing germs.

Examples of cell wall lysing enzymes are endolysins, which were isolated from bacteriophages. Bacteriophages use these enzymes at the end of their cycle of propagation to release the bacteriophages which were produced inside the bacterial cell. Thereby the bacterial shell is lysed and the host bacterium is destroyed in that way. A further example are enzymes, which the bacteriophage requires at the beginning of its cycle of propagation and are localized normally in bacteriophage tail proteins. These enzymes are required for the break up of the bacterial wall in the bacterial infection. A third example are enzymes, which have a similar function and often also a sequence similarity to the endolysins. These enzymes are autolysins produced under certain circumstances by bacteria leading to the self-lysis of the bacteria. A forth example are enzymes, which are also produced by bacteria and are known as bacteriocins. These four groups of cell wall lysing enzymes are already technically deployed and yet gain in importance in the future.

One field of application is the medical utilisation in the prevention and therapy as well as the diagnostic of bacterial infections in human and animals. A further field of application is the use in the food, environmental and cosmetic industry for prevention of a unexpected bacterial growth and for killing of the germs for example by disinfection, as well as the detection of bacteria in food, environmental and cosmetic samples.

Virtually all applications, in which bacteria lysing enzymes are used, impose high requirements for the stability of the used enzymes, so that their use is economically profitable. In the U.S. Pat. No. 6,432,444 B1 for stabilization of the cell wall lysing enzymes it is proposed to use for example a stabilizing buffer to assure the optimal enzyme activity. Moreover the addition of stabilizing substances like reducing agents, metal chelators, immune globulins, specific buffer salts, physiological pH values, preservatives or mild detergents are proposed.

Generally the stability of proteins is often reduced by existing proteases. Strategies for increasing the stability of proteins to protease degradation are, e.g. the addition of metal chelators, to inhibit proteases, which require metal ions for their activity or the addition of special protease inhibitors, as they are commercially available for serine proteases. However protease inhibitors could be only limited used for stabilizing of cell wall lysing enzymes, because they disturb also other essential components at the target site. Furthermore specific inhibitors are also expensive. Also the choice of other environmental conditions, in which the proteases are less active, are normally not possible, because the cell wall lysing enzymes require very similar conditions for their activity as the proteases. Thus, cell wall lysing enzymes operate best in an aqueous environment and under moderate pH values, under which also the protease activity is highest. The known stabilizing methods are not appropriate for the use of cell wall lysing enzymes.

Thus the object of the present invention is to provide stable cell wall lysing enzymes.

The object is solved by the subject matter as defined in the claims.

The following figures illustrate the invention.

FIG. 1 shows the wild type amino acid sequence (SEQ ID NO: 20) of the CHAP domain (amino acid 1-154), the linker region (underlined, amino acid 155-193) and the amidase domain (amino acid 194-393) of an endolysin from PlyPitti26. Potential cleavage sites for V8 protease cleaving after the amino acid residue E, are highlighted in bolt and are located at the amino acid positions 163, 179 and 189. The thrombin cleavage site is highlighted in grey and located at position R167.

FIG. 2 shows the result of a protease digest and following activity test of non modified PlyPitti26 with the proteases thrombin and V8 protease. FIG. 2A shows a SDS polyacrylamide gel with samples of non modified PlyPitti26 after a digest with thrombin (T), V8 protease (V8) and a control digest with plasmin (P), for which exists no cleavage site. Undigested PlyPitti26 is marked with "-". M describes molecular weight standards with the protein sizes given in kDa in the right-hand margin. In the right-hand margin the position of the bands for the fragment N-terminal of the thrombin cleavage site (CHAP domain), the fragment C-terminal of the cleavage site (ami-CBD) and the band of the added thrombin are given. FIG. 2B shows the result of a liquid lysis test for determination of the specific activities of digested and non-digested non-modified PlyPitti26. The bacteria cell lysis is monitored by a light scattering measurement in the photometer. The lysis curves are illustrated for undigested PlyPitti26 (_____) plasmin digested (-----) as well as with thrombin (_._._.) or V8 protease (_.._..) digested endolysin.

FIG. 3 shows the result of a protease digest of modified and non-modified CHAP-AmiPitti26-CBDUSA. FIG. 3A shows the result of a thrombin digest of the non-modified CHAP-AmiPitti26-CBDUSA and of a modified *Staphylococcus* endolysin CHAP-AmiPitti26-CBDUSA (Mutant 4 in table 3). The non-modified CHAP-AmiPitti26-CBDUSA has a singular thrombin cleavage site between the CHAP— and the amidase domain at position R167, the modified polypeptide has a substitution from R to A at position 167. The FIG. 3A shows a SDS polyacrylamide gel of both enzyme variants before and after the thrombin digest: M-molecular weight marker (molecular weights given in kDa in the margin); 1-non-modified CHAP-AmiPitti26-CBDUSA without thrombin; 2—non-modified CHAP-AmiPitti26-CBDUSA after thrombin digest: 3—modified CHAP-AmiPitti26-CBDUSA without thrombin; 4—modified CHAP-AmiPitti26-CBDUSA after thrombin addition.

FIG. 3B shows the result of a V8 protease digest of the non-modified CHAP-AmiPitti26-CBDUSA and a modified *Staphylococcus* endolysin CHAP-AmiPitti26-CBDUSA (mutant 4 in table 3). The non-modified CHAP-AmiPitti26-CBDUSA has a V8 protease cleavage site between the CHAP- and the amidase domain at position R163, the modified polypeptide has a substitution from E to A at position 163. The FIG. 3B shows a SDS polyacrylamide gel of both enzyme variants before and after the V8 protease digest: M-molecular weight marker (molecular weights given in kDa in the margin); 1-non-modified CHAP-AmiPitti26-CBDUSA without V8 protease; 2—non-modified CHAP-AmiPitti26-CBDUSA 15 min V8 protease digest: 3—non-modified CHAP-AmiPitti26-CBDUSA 60 min V8 protease digest; 4—modified CHAP-AmiPitti26-CBDUSA without V8 protease; 5—modified CHAP-AmiPitti26-CBDUSA 15 min V8 protease digest; 6—modified CHAP-AmiPitti26-CBDUSA 60 min V8 protease digest.

FIG. 4 shows an amino acid sequence comparison of the modified endolysins from the *Cl. difficile* phage Φ CD119 (CD119) (SEQ ID NO: 5) with the modified endolysin from the *Cl. difficile* phage Φ630(SEQ ID NO: 4). The singular caspase 1 cleavage site at amino acid D214 existing in the Φ CD119 and Φ630 wild type was modified to E214, the singular thrombin cleavage site R87 existing in the Φ630 wild type was modified to K87.

FIG. 5 shows an amino acid sequence comparison of the region of the thrombin cleavage site of various *Staphylococcus aureus* endolysins (SEQ ID NO: 23). The bolt highlighted amino acid residue R is position R167 in the reference sequence ply_pitti26, described as P26A. The further listed amino acid sequences are aligned with R167 of ply_pitti26. The amino acid sequence comparison was performed with the program BLAST; Altschul et al., 1990, J. Mol: Biol., 215, 403-410. The number to the right of the amino acid sequence comparison describes the amino acid position of the last amino acid in the represented sequence segment of the respective endolysin. The numbers in the left margin stands for different homologous proteins from the amino acid sequence comparison. P26A stands for ply_pitti26, 15 an autolysin (N-acetylmuramoyl-L-alanine amidase) from *Staphylococcus aureus* (database accession number P24556), 16 stands for an amidase from the bacteriophage 80 alpha (database accession number AAB39699), 3 stands for the endolysin of *Staphylococcus* phage phi MR11 (database accession number YP 001604156), 4 stands for ORF006 from the *Staphylococcus aureus* phage 88 (database accession number YP240699), 5 stands for ORF21 from the *Staphylococcus aureus* phage 85 (database accession number YP239752), 9 stands for the amidase from the *Staphylococcus* phage 11 (database accession number NP803306), 10 stands for ORF007 from the *Staphylococcus* phage 52A (database accession number YP240634), 11 stands for the N-acetylmuramoyl-L-alanine amidase from the strain *Staphylococcus aureus* subsp. *aureus* JH9 (database accession number YP 001246457), 12 stands for a putative cell wall hydrolase of the phage phiMR25 (database accession number YP 001949866), 13 stands for ORF007 from the *Staphylococcus* phage 69 (database accession number YP 239596), 14 stands for ORF007 from the *Staphylococcus* phage 55 (database accession number YP 240484), 2 stands for the N-acetylmuramoyl-L-alanine amidase form the strain *Staphylococcus aureus* subsp. *aureus* NCTC 8325 (database accession number YP 500516), 1 stands for the amidase from the *Staphylococcus* phage phiNM2 (database accession number ABF73160), 6 stands for a phage-related amidase form the strain *Staphylococcus aureus* RF122 (database accession number YP 417165), 17 stands for ORF006 from the *Staphylococcus* phage 37 (database accession number YP 240103) and 18 stands for ORF007 from the *Staphylococcus* phage EW (database accession number YP 240182).

FIG. 6 represents amino acid sequences of modified and non-modified CHAP-AmiPitti26-CBDUSA. FIG. 6 A to D shows the amino acid sequence of CHAP-AmiPitti26-CBDUSA without amino acid substitutions at protease cleavage sites (A) (SEQ ID NO: 18) and CHAP-AmiPitti26-CBDUSA with amino acid substitutions at protease cleavage sites (B to E). Sequence in FIG. 6B is SEQ ID NO: 2, FIG. 6C is SEQ ID NO: 3, FIG. 6D is SEQ ID NO: 1, FIG. 6E is SEQ ID NO: 11, FIG. 6 F to K shows the amino acid sequence of CHAP-AmiPitti26-CBDUSA-Add2 without amino acid substitutions at protease cleavage sites and an additional amino acid residue at position two (F) (SEQ ID NO: 19) and CHAP-AmiPitti26-CBDUSA-Add2 with amino acid substitutions at protease cleavage sites and an additional amino acid residue at position two (G to K). Sequence in FIG. 6G is SEQ ID NO: 15, FIG. 6H is SEQ ID NO: 16, FIG. 6I is SEQ ID NO: 14, FIG.6K is SEQ ID NO: 17.

FIG. 7 A shows the amino acid sequence of the modified endolysin form the *Cl. difficile* strain 630 with a substitution of D214 to E214 (SEQ ID NO 4). FIG. 7B shows the amino acid sequence of the modified *Cl. difficile* endolysin from the phage phi CD119 with a substitution of R87 to K87 and D214 to E214 (SEQ ID NO: 5).

FIG. 8 shows an amino acid sequence of the endolysin Ply511 (SEQ ID NO: 6). The amino acid positions E7, E40 and E89 printed in bold could be substituted with any other amino acid residue.

FIG. 9 shows the amino acid sequence of the endolysin Ply511 (SEQ ID NO: 5). The potential cleavage sites(R in P1 position) for the protease clostripain are underlined. The both experimentally determined particularly sensible cleavage sites (R92 and R221) are underlined and printed in bolt.

FIG. 10 shows the digest of the therapeutically used endolysin CHAP-Amipitti26_CBDUSA-Add2 (L56H, L57T, E164A, R168A, Y201H) by proteases existing in organ extracts. FIG. 10 A shows a SDS gel, in which the protein bands are separated after incubation with liver, kidney and lungs extract. On the left a molecular weight standard is loaded. Lines 1 to 3 show controls (only endolysin, no organ extract), which were incubated not at all (line 1), 18 h at room temperature (line 2) or 18 h at 4° C. (line 3). In the lines 4 to 6 liver extract was added, in line 7 to 9 kidney extract and in the lines 10 to 12 lungs extract. Lines 4, 7 and 10 only contain organ extract, lines 5, 8 and 11 organ extract and endolysin after 18 h incubation at room temperature, lines 6, 9 and 12 organ extract and endolysin after 18 h incubation at 4° C. The arrows with the numbers 1 to 7 beside line 9 mark the bands, which were N-terminally sequenced after transfer on a blot membrane. FIG. 10 B shows a SDS gel, on which the protein bands were separated after incubation with heart or spleen extract. On the left a molecular weight standard is loaded. Lines 1 to 3 as well as 10 show controls (only endolysin, no organ extract), which were incubated not at all (line 1 to 10), 18 h at room temperature (line 2) or 18 h at 4° C. (line 3). In the lines 4 to 6 heart extract was added, in line 7 to 9 spleen extract. Lines 4 and 7 only contain organ extract, lines 5 and 8 organ extract and endolysin after 18 h incubation at room temperature, lines 6 and 9 organ extranct and endolysin after 18 h incubation at 4° C.

FIG. 11 shows the sequence of the endolysin CHAP-Amipitti26_CBDUSA-Add2 (L56H, L57T, E164A, R168A, Y201H) with protease sensitive regions (SEQ ID NO: 22). The cleavage sites (P1position), which resulted from the incubation with kidney extract, are highlighted in bolt. Amino acid sequences, which resulted from the N-terminal sequencing of the produced fragments, are underlined. Amino acid regions defining the domain linker are presented in italic. This is a domain linker region between the CHAP and amidase 2 domain (amino acids 159 to 198) as well as a second linker between the amidase 2 domain and the CBD (amino acids 347 to 412).

FIG. 12 shows an amino acid sequence comparison of the region of the caspase I cleavage site of different *Staphylococcus* endolysins (SEQ ID NO: 24). It is a matter of amidases from the *Staphylococcus* phage SAP-2, 44AHJD and phage 66. The NCBI database accession numbers for the proteins are YP_001491539, 44AHJD_15 amidase and YP_239469. The position D42, after which it is cleaved, is highlighted in bolt, the conservative recognition sequence of the caspase I is represented each in italic and framed. The three proteins are identical from 89 to 90% from their whole length, not conservative amino acids for the region of the amino acids 1 to 60 are marked with "-". The amino acid sequence comparison was performed with the program BLAST.

The term "polypeptide" or "protein" as used herein describes peptides of at least eight amino acids. The polypeptide may be pharmacologically or immunologically active polypeptides or polypeptides used for diagnostic purposes.

The term "cell wall lysing enzymes" as used herein describes enzymes, which are capable, to at least partially break up or thus damage the bacterial cell wall that as a result a cell lysis or at least a bacteriostatic effect arises. Particularly the term describes endolysins, autolysins, bacteriophage tail proteins and bacteriocins.

The term "endolysin" as used herein describes enzymes, which are encoded naturally by bacteriophages and which are produced by them at the end of their host cycle to lyse the host cell and thus, releasing the bacteriophages newly produced in the host cells. Endolysins are built of at least an enzymatically active domain (EAD) and a non-enzymatically active cell binding domain (CBD). The single EADs have different activities, wherein endolysins have at least one EAD selected from the following group: N-acetyl muramoyl-L-alanine amidase (amidase, e.g. Ami_2, Ami_5), (endo)-peptidase (e.g. CHAP, i.e. cysteine, histidine-dependent amidohydrolases/peptidases), transglycosylase, glycosylhydrolase, (N-acetyl)-muramidase (lysozymes) and N-acetyl-glucosaminidase.

The term "autolysin" as used herein describes bacterial peptidoglycan hydrolases leading to a self-lysis of the bacteria in particular situations. Autolysins and endolysins are often functionally and structurally related. Different domains from endolysins and autolysins may be often modular combined and form active chimera.

The term "bacteriophage tail protein" as used herein describes structural phage proteins, which in the beginning of the replication cycle of the bacteriophage in the infection fulfil the function to bind receptors on the bacteria surface and thereby lyse components on the cell surface via their enzymatic function. The respective bacteriophage proteins do not always have to be located in the phage tail, but may also sit directly at the phage head in phages without tail.

The term "bacteriocin" as used herein describes proteinogenic toxins, which are secreted from bacteria to inhibit the size growth of similar bacterial genus. They consist of a cell wall binding domain, a translocation domain and of the "killing factor". The group of the bacteriocins contained in this connection thereby attacks bacterial membranes. Examples are colicin, microcin, nisin, epidermin and lantibiotics (lanthionine-containing antibiotics).

The term bacterial "cell wall" as used herein describes all components forming the outer cell envelope of the bacteria and thus guarantees their integrity. Particularly it refers to the peptidoglycan, the outer membrane of the Gram-negative bacteria with the lipopolysaccharide, the bacteria cell membrane, but also layers additionally supported on the peptidoglycan like capsules, mucous or outer protein layers.

The term "protease" as used herein describes an enzyme, which is capable to hydrolytically cleave proteins and/or peptides.

The term "domain" as used herein describes a part of an amino acid sequence which is defined functionally and/or structurally. Domains often may be predicted very well due to homologies via respective search programs, which are based on respective databases with conserved domains (e.g. Conserved Domain Database (CDD) at the NCBI (Marchler-Bauer et al., 2005, Nucleic Acids Res. 33, D192-6), Pfam (Finn et al., 2006, Nucleic Acids Research 34, D247-D251) or SMART (Schultz et al., 1998, Proc. Natl. Acad. Sci. USA 95, 5857-5864, Letunic et al., 2006, Nucleic Acids Res 34, D257-260).

The term "wild type" as used herein describes the amino acid sequence, as she occurs in naturally occurring proteins and whose sequence was not modified in regard to protease cleavage sites. These might be amino acid sequences as naturally occurring in a bacteriophage, prophage or bacterium. Additionally the term means all amino acid sequences of cell wall lysing enzymes existing in databases, which contain specific protease cleavage sites yet, even though the amino acid sequences were already modified compared with naturally existing proteins. In connection with nucleotide sequences the term wild type means also the nucleotide sequences encoding a polypeptide, which have an above-described amino acid sequence.

The present invention relates to a modified polypeptide with the biological activity to lyse cell walls of bacteria, wherein the polypeptide contains no caspase, enterokinase, factor Xa, granzyme B, *staphylococcus* peptidase I (V8 protease), plasmin, streptopain, bacillolysin or thrombin cleavage site as well as further protease cleavage sites, which were specific for each polypeptide determined by protease digest with subsequent analysis of the formed fragments and afterwards were modified in that way described in the invention. Preferably the present invention relates to modified polypeptides according to the present invention, which lyse Gram-positive bacteria, whereas the bacteria may derive from the group consisting of clostridia, *listeria*, staphylococci, lactobacilli, enterococci, aerococci, pediococci, streptococci, mycoplasms and/or *leuconostoc*. Preferably the polypeptide of the invention is an endolysin, a bacteriophage tail protein, an autolysin or a bacteriocin.

The present invention further relates to a recombinantly produced polypeptide with a biological activity to lyse cell walls of bacteria, wherein the amino acid sequence of the polypeptide compared to the wild type sequence has modifications at amino acid positions, which are recognized by proteases and/or after which the proteases cleave the polypeptides.

Surprisingly it turned out that the cell wall lysing enzymes may be modified in such a way in their amino acid sequence, that an increased protease stability may be achieved, without stabilizing substances have to be added. It is generally known that different proteases cleave the polypeptide chain at a specific amino acid residue or require amino acid sequence motifs for their enzymatic activity. Protease cleavage sites in proteins may be predicted with respective sequence analysis programs in case of existing amino acid sequence (e.g. ExPASy, PeptideCutter, Gasteiger et al., Protein Identification and Analysis Tools on the ExPASy server in John M. Walker (ed): The Proteomics Protocols Handbook, Humana Press (2005)). Thus, it results normally in far more than 100 potential protease cleavage sites for a protein of medium size with approximately 300 to 400 amino acid residues, so that a stabilization of proteins is only to be achieved by modifying the cleavage sites of a plurality of proteases. But this is impracticable because the protein looses its effect and activity if to much amino acid modifications are introduced. A further possibility for determination of protease sensitive regions beside the prediction by means of the amino acid sequence, especially for proteases, in which no recognition sequence is known or their identity is not known, is the experimental determination of the actually cleavage sites by a digest of the proteins with commercially available proteases. Further isolated proteases from organisms or samples may be used therefore. Particularly the samples, which contain the proteases such as food samples, environmental samples, organ extracts, medical samples may be used without isolating the proteases before. Subsequent the assays are subjected to an analysis of the formed degradation products by means of sequence determination (e.g. N- or C-terminal sequencing, peptide mapping in connection with mass spectrometry) and size determination (e.g. mass spectrometry, band analysis of SDS gels, analytical gel filtration). Actually the inventors have found cleavage sites and amino acid sequence motifs for proteases in many cell wall lysing enzymes. This occurs surprisingly, whether it is assumed that the cell wall lysing enzymes must be evolved to a high stability. Surprisingly it became apparent, however, that the cleavage sites and amino acid sequence motifs for the proteases are in small number, often even in singular form in the cell wall lysing enzymes and often also are conserved in homologous proteins. As a result a modification of just a few or even only one protease cleavage site is sufficient to increase the stability of the cell wall lysing enzymes.

In the present invention preferably only such protease cleavage sites are modified, which are recognized by specific proteases potentially existing at the target site of the cell wall lysing enzymes. Thereby the amino acid sequences of the cell wall lysing enzymes are modified, that they are no longer recognized by the specific proteases and thus are no longer cleaved. This leads to an increased stability of the cell wall lysing enzymes towards proteases existing at the target site. Thus, a protease caused loss of activity of the cell wall lysing enzymes is prevented and a longer effectiveness is achieved.

There are a series of proteases, which require a specific recognition sequence in their substrate proteins for their enzymatic activity. Several examples therefore are presented in the following table. A plurality of further proteases is known by the person skilled in the art like they are described for example in the Merops peptidase database (Rawlings et al., 2008, Nucleic Acids Res 36, D320-D325). The following, however, also applies to protease cleavage sites of unknown proteases, which may be experimentally determined. P1 describes the position of the amino acid, after which it is cleaved, P4, P3 and P2 are the positions N-terminal before the cleavage site P1. The description P1' und P2' are the positions C-terminal following P1. This means that the proteases cleave the polypeptide chain between P1 and P1'. The capitals presented instead of the amino acid residues represent the international used description of the amino acid residues and are generally known. If the capitals are used in the description of the present invention, the respective amino acid residues are meant.

TABLE 1

| Protease | Cleavage site | | | | | |
|---|---|---|---|---|---|---|
| | P4 | P3 | P2 | P1 | P1` | P2` |
| Caspase 1 | F, W, Y or L | — | H, A oder T | D | not P, E, D, Q, K or R | — |
| Caspase 2 | D | V | A | D | not P, E, D, Q, K or R | — |
| Caspase 3 | D | M | Q | D | not P, E, D, Q, K or R | — |
| Caspase 4 | L | E | V | D | not P, E, D, Q, K or R | — |
| Caspase 5 | L or W | E | H | D | — | — |
| Caspase 6 | V | E | H or I | D | not P, E, D, Q, K or R | — |
| Caspase 7 | D | E | V | D | not P, E, D, Q, K or R | — |
| Caspase 8 | I or L | E | T | D | not P, E, D, Q, K or R | — |
| Caspase 9 | L | E | H | D | — | — |
| Caspase 10 | I | E | A | D | — | — |
| Clostripain (Clostridiopeptidase B) | — | — | — | R | — | — |
| Enterokinase | D or N | D or N | D or N | K | — | — |
| Factor Xa | A, F, G, I, L, T, V or M | D or E | G | R | — | — |
| Plasmin (Fibrinolysin, Fibrinase) | — | — | — | K or R | — | — |
| Streptopain (Streptococcus Peptidase A) | — | — | F | F | Y | — |
| Bacillolysin (Bacillus subtilis neutral Protease) | — | G or F or A | G or F | L or F | A or G or L | — |

TABLE 1-continued

| | Cleavage site | | | | | |
|---|---|---|---|---|---|---|
| Protease | P4 | P3 | P2 | P1 | P1` | P2` |
| Granzyme B | I | E | P | D | — | — |
| Staphylococcus peptidase I (V8 Protease) | — | — | not E | E | — | — |
| Thrombin | — | — | G | R | G | — |
| | A, F, G, I, L, T, V or M | A, F, G, I, L, T, V, W or A | P | R | not D, E | not D, E |

Preferably the present invention relates to a modified polypeptide with a biological activity to lyse cell walls of bacteria, wherein the polypeptide according to the present invention has compared to the naturally occurring polypeptide one or more modifications in its amino acid sequence at one or more positions shown in table 1 or in experimentally determined protease cleavage sites, wherein the one modification or the several modifications occur at amino acids of protease cleavage sites shown in table 1 or experimentally determined. Thus the stability of the polypeptide increases towards the protease or proteases, whose recognition sequence was changed respectively.

In a preferred embodiment of the present invention the amino acid residue is substituted by another appropriate amino acid residue at the position, after which it is cleaved (P1), so that the polypeptide of the invention is no longer cleaved by the protease whose recognition site was modified respectively. Instead of a substitution of the amino acid residue at position P1 or also additional to a substitution at position P1 further amino acid residues in the recognition site may be substituted, preferably the positions at P4, P3, P2, P1' and/or P2' presented in table 1, by other amino acid residues. Preferably 6, 5, 4, 3, 2, 1 substitutions per recognition site are performed, more preferably in particular 1 to 3 substitutions.

In a further embodiment of the present invention one or more protease cleavage sites in a polypeptide, as previously described, may be modified.

It is important, that the protein variant according to the present invention after the mutation do not only have a higher stability to protease degradation, but also further retain its cell wall lysing activity. Thus, the amino acid substitution is performed as described below.

In the state of the art a series of essential amino acid residues are known, which are known for the activity of the cell wall lysing enzymes, e.g. conserved cysteines and histidines in different amidases or CHAP domains. The respective essential residues may also be found with sequence analysis programs, which specifically search for conserved domains (e.g. Conserved Domain Database (CDD) via NCBI (Marchler-Bauer et al., 2005, Nucleic Acids Res. 33, D192-6), Pfam (Finn et al., 2006, Nucleic Acids Research 34, D247-D251) or SMART (Schultz et al., 1998, Proc. Natl. Acad. Sci. USA 95, 5857-5864, Letunic et al., 2006, Nucleic Acids Res 34, D257-D260).

To little destabilize the stability, structure and function of the polypeptides according to the present invention as possible, the amino acid residues of the protease recognition sequence to be substituted are substituted by amino acid residues, which are closely related by their structure and biochemistry as possible and however are not recognized by the protease. In the meantime it is general specialist knowledge to assign the 20 naturally occurring amino acids in specific groups, which differ in their biochemistry (e.g. acid, basic, hydrophobic, polar, aromatic amino acids), but within which the amino acids are related to each other. Preferred substitutions for the amino acid residues in the polypeptides of the invention are summarized in table 2. The substitution possibilities mentioned in column 2 are conservative amino acid alternatives, which are especially similar to the amino acid residue in the wild type either by their structure and/or their function. These are more preferred substitution variants. However, further substitution variants are also possible for the cell wall lysing polypeptides of the present invention, which are mentioned in column 3.

TABLE 2

| Amino acid in the wild type | Conservative substitution | Further substitution possibilities |
|---|---|---|
| A (Ala) | S | T, G, V, E, D |
| N (Asn) | Q, D | K, H, I, T, S, A |
| D (Asp) | E, N | A, G, S |
| R (Arg) | K | S, Q, A |
| C (Cys) | S | M, G, A |
| E (Glu) | D, Q | A, G, S, A |
| Q (Gln) | N, E | H, L, R, A |
| G (Gly) | A | S, N, D |
| H (His) | Q, N | R, A |
| I (Ile) | V, L | T, A |
| L (Leu) | V, I | M, F, A |
| K (Lys) | R | N, T, S, Q, A |
| M (Met) | L | K, V, I, C, A |
| F (Phe) | Y | L, I, M, A |
| P (Pro) | A | S, Q |
| S (Ser) | A, T | G, N, K |
| T (Thr) | S, A | V, K, N |
| W (Trp) | Y | F, S, R, A |
| Y (Tyr) | F | H, N, C, A |
| V (Val) | I, A | L, T |

A further possibility to determine, which amino acid residue is integrated instead of the residue to be substituted, represents the Dayhoff-Matrix; see for example in Creighton (Proteins: Structure and Molecular Properties, $2^{nd}$ Ed., 1984, Freeman, N.Y.). From studies of homologous proteins it is known, that the mere statistically random mutation on nucleic acid level is not reflected in the amino acid sequence of the respective proteins. Thus, it seems to exist a selection pressure on specific amino acid residues for specific amino acid positions in the homologous proteins, what is given in the Dayhoff-Matrix.

A further possibility to determine which amino acid residue is integrated instead of the residue to be substituted, employs the assistance of sequence analysis programs, e.g. the program BLAST, see Altschul et al., 1990, J. Mol. Biol., 215, 403-410. So, it may be searched for proteins related to the cell wall lysing enzymes to be mutated. Thereby the search algorithm finds similarities on sequence level. If it is searched on amino acid sequence level, the program "Protein BLAST" is suitable to show functional and/or evolutionary relationships. Whether amino acid variants with at least about 60% or at least about 80% or at least about 90% identity are found in a region of about 100 or 50 or 20 amino acid residues as limit around the potential protease cleavage site, the amino acid sequence, which differs from the protease recognition sequence may be integrated in the polypeptide of the present invention. Thereby the amino acid substitutions may differ from the substitution possibilities represented in table 2.

There are a series of known endolysins having protease cleavage sites, as represented in table 1, in particular cleavage sites for the proteases thrombin, caspase, clostripain or V8 protease. Particularly thrombin- or caspase cleavage sites are often singular and may be substituted according to the present invention resulting in a stabilized endolysin. In a preferred embodiment the polypeptide of the present invention is modified in one or more thrombin recognition sequences. Thereby the amino acid residue at position P1 described by R is substituted with the amino acid residue described by K. A substitution against S, Q or A is also preferred. In the first variant of the thrombin recognition sequence (G; R; G) both G or only one thereof may be substituted with preferably A additionally or alternative to the substitution of the R. In the second variant of the thrombin recognition sequence (P; R; not D, E; not D, E) preferably also the R is substituted with a K or with a S, Q or A. Further one or both positions P1' and P2' may be substituted with a D or E additionally or as alternative.

In a further preferred embodiment the amino acid residue D at the position P1 of a caspase cleavage site is substituted with N or A. The amino acid residue R at the P1 position of a clostripain cleavage site is preferably substituted with K or A, the amino acid residue E at the P1 position of a V8 protease cleavage site with Q or A. Further preferred substitutions are summarized in table 2, stabilizing substitution in the recognition site beyond the P1 position may also be performed.

More preferred embodiments are given in SEQ ID NO: 1, 2, 3, 4 and 5.

The present invention further relates to a recombinantly produced polypeptide with the biological activity to lyse cell walls of bacteria, wherein the amino acid sequence of the polypeptide has amino acid additions compared to the wild type sequence. Preferably the polypeptide of the invention has one, two, three or four additions of amino acid residues, wherein the amino acid residues may be introduced coherently or independently of each other. Preferred is the addition of one or two amino acid residues, particularly preferred is the addition of an amino acid residue at position two. The amino acid additions may be introduced in polypeptides, which have modifications at amino acid positions, which are recognized by proteases and/or after which the proteases cleave the polypeptides or also in polypeptides, in which such modifications were not integrated. Particularly preferred embodiments are given in SEQ ID NO: 12-17, 19 and 22.

In a further preferred embodiment the polypeptide of the invention is modified in one or more V8 protease recognition sequences. Thereby the amino acid residue described by E at position P1 is substituted with another amino acid residue preferably with the amino acid residue described by A or Q. A particularly preferred embodiment is given in SEQ ID NO: 6.

In a further preferred embodiment the polypeptide of the invention is modified in one or more clostripain cleavage sites. Thereby the amino acid residue described by R at position P1 is substituted with another amino acid residue preferably with the amino acid residue described by K or A. Particularly preferred embodiments are given in SEQ ID NO: 7 and 8.

In a further preferred embodiment the polypeptide of the invention is modified in one or more caspase recognition sequences. Thereby the amino acid residue described by D at position P1 is substituted with another amino acid residue preferably with the amino acid residue described by E or A. Particularly preferred embodiments are given in SEQ ID NO: 9 and 10.

In a further preferred embodiment the polypeptide of the invention is modified in one or more V8 protease recognition sequences and one or more thrombin recognition sequences. Thereby the amino acid residue at position P1 described by E is substituted with another amino acid residue preferably against the amino acid residue described by Q or A and the amino acid residue at position P1 described by R is substituted with another amino acid residue preferably against the amino acid residue described by K or A. A particularly preferred embodiment is given in SEQ ID NO: 11.

In a further preferred embodiment the polypeptide of the invention is modified in one or more protease recognition sequences, which were identified after a digest with kidney extract. Thereby the amino acid residue at position P1 described by Q is substituted with another amino acid residue preferably against the amino acid residue described by N or A and the amino acid residue at position P1 described by S is substituted with another amino acid residue preferably against the amino acid residue described by T or A. Particularly preferred embodiments are given in SEQ ID NO: 12 and 13.

The amino acid substitutions introduced within the scope of the present invention may be performed by means of molecular biological standard techniques which are known by the person skilled in the art and are given for example in Sambrook et al., Molecular cloning. A laboratory manual; $2^{nd}$ ed. Cold Spring Harbor Laboratory Press 1989. Thus, by means of DNA primers the desired mutations may be integrated into the nucleic acid sequence encoding the polypeptide of the invention. The modified nucleotide sequences thereby obtained may be then expressed in an appropriate host, preferably *E. coli*, and the polypeptides are purified. The nucleotide sequence encoding the polypeptide of the invention further may be amended with the so-called codon usage to the respective host cell to achieve a better expression. The present invention relates to the nucleotide sequence encoding the polypeptide of the invention, respective expression vectors and host cells for the production of the polypeptide according to the invention.

The polypeptides of the invention may be investigated with different tests for protease sensitivity and/or enzyme activity. Examples for such tests are protease digest and subsequent separation of the fragments by SDS gel electrophoresis, mass spectrometry, cell lysis test on agar plates, liquid lysis test by measuring the light scattering in the photometer, zymogram assay for activity test on gels.

The polypeptides of the invention may be used in medical, therapeutical, diagnostical, environmental, cosmetic or food sector.

The present invention further relates to a nucleic acid molecule, comprising a nucleotide sequence encoding a polypeptide of the invention. The present invention further relates to a vector, comprising a nucleic acid molecule of the invention.

Further the present invention relates to appropriate host cells for the expression of the polypeptides according to the invention. Preferably an appropriate host cell for the expression of the polypeptides according to the invention comprises a nucleic acid molecule according to the invention or a vector according to the invention. Preferably an appropriate host cell for the expression of the polypeptides according to the invention is transformed with a nucleic acid molecule according to the invention.

In the modification of the recognition sites thereby preferably the recognition site of such proteases is modified, which occur from experience in the desired field of application. Thus, it is known, that in human or in animals for example the caspases, thrombin, granzyme B, enterokinase, factor Xa occur. Tissue specific proteases, e.g. the proteases meprin and rennin, occurring in the kidney are known by the person skilled in the art. Further proteases from pathogenic bacteria may be additionally available, which cause an infection in human or animal or which are present as secondary flora. These include for example the V8 protease from *Staphylococcus* or clostridiopeptidase B from clostridia. If the polypeptides of the invention should be used in the therapy of such infection, preferably the recognition sites for the proteases are modified, which are present in bacteria being responsible for the infection to be treated.

Preferably the protease sensitive regions of the cell wall lysing enzymes are determined experimentally by a digest of the proteins with commercially available proteases, isolated proteases from organisms or samples containing proteases, such as food samples, environmental samples, organ extracts, medical samples and a subsequent analysis of the resulting degradation products by means of sequence determination (e.g. N- or C-terminal sequencing, peptide mapping in connection with mass spectrometry) and determination of the size (e.g. mass spectrometry, analysis of bands of SDS gels, analytical gel filtration). One field of application for cell wall lysing enzymes is the topical application in wounds in form of ointments, creams, tinctures or wound dressings like dressings and bandages, e.g. in case of infections by staphylococci or clostridia. Additional stability problems for the cell wall lysing enzymes may occur by the fact that, in the wound care partially medicaments or medical products are used, which also contain proteases. For example it is tried in wounds of the skin to achieve a gentle wound cleaning by fibrinolysis. Examples for proteases which are used in the wound care, are fibrinolysin, plasmin, streptokinase, clostridiopeptidase A and *Bacillus subtilis* protease. Preferably the polypeptides of the invention have also modifications of the recognition sites for these proteases.

In the food, environmental and cosmetic industry a plurality of proteases may also be present, which are produced either by bacteria used for example in the food production, like lactobacilli, lactococci or different bacilli strains, or which are excreted by undesirable germs, which should be lysed (e.g. *B. cereus, B. subtilis, Cl. perfringens, Cl. botulinum*). In bacteria used in the food production, such as *Lactobacillus acidophilus, L. casei, L. delbrueckii, L. brevis, L. helveticus* or *Lactococcus* lactis for example each between 60 and 130 proteases are known. Additionally proteases are also present in the food itself Preferably the polypeptides of the invention have such modifications of the recognition sites of proteases, which occur in the food, environmental and cosmetic industry.

The present invention further relates to the polypeptide of the invention as medicament or a pharmaceutical composition as well as the use of the polypeptide of the invention as medicament or pharmaceutical composition for prevention or therapy of diseases, which are caused by Gram-positive bacteria, particularly clostridia, bacilli, *listeria*, staphylococci, lactobacilli, enterococci, aerococci, pediococci, streptococci, mycoplasms and/or *leuconostoc*.

The present invention further relates to the polypeptide of the invention as a diagnostic agent or diagnostic composition as well as the use of the polypeptide of the invention as a diagnostic agent or diagnostic composition in the medicine for detection of diseases, in particular which are caused by Gram-positive bacteria, particularly clostridia, bacilli, *listeria*, staphylococci, lactobacilli, enterococci, aerococci, pediococci, streptococci, mycoplasms and/or *leuconostoc*.

The polypeptide of the invention is used in the diagnostic to specifically lyse the bacteria to be detected, so that one or more detection steps may follow, which detect specific cell components of the bacteria, like DNA, RNA, enzymes, cell wall components. The appropriate methods therefore, e.g. PCR, NASBA, hybridization, antibody based detections like ELISA, biochemical detections for certain specific enzymes, colorimetric detections are known in the state of the art.

Furthermore the present invention relates to the use of the polypeptide of the invention for inhibiting the growth of the detection of Gram-positive bacteria in the environmental, food or cosmetic industry.

The following examples are provided merely by way of explanation, but in no sense restrict the scope of invention.

EXAMPLE 1

Protease Digest of PlyPitti26

It was performed a digest of PlyPitti26 with the proteases thrombin and V8. Each 90 µl protein solution (protein concentration 1.35 mg/ml) were tampered with 10 µl thrombin and in control samples only tempered with plasmin. For the V8 protease digest 99 µl protein solution and 1 µl protease solution were used. The concentration of the protease stock solutions was each 500 µg/ml. The samples were incubated in a 20 mM Tris/HCl pH 7.5, 10 mM DTE, 0.1 mM $ZnSO_4$ Buffer over night at 25° C. A part of the samples was tempered with SDS gel-application buffer and was analysed on SDS polyacrylamide gels after boiling.

It was found that PlyPitti26 is degraded completely by thrombin, wherein two relative large protein fragments emerged, of which the one contained the CHAP-domain and the other the amidase domain and the CBD. In a digest with V8 protease several smaller, but also defined protein fragments emerged. In a control digest with plasmin no fragmentation of the protein occurs under the given conditions. The results are shown in FIG. 2A.

EXAMPLE 2

Activity Test of Untreated PlyPitti26 and PlyPitti26 Treated with Proteases

In further experiments the samples were tested in the liquid lysis test on the lysis activity towards *Staphylococcus* cells. The liquid lysis test is an activity test for cell wall lysing enzymes, in which the bacterial cell lysis was measured in real time via light scattering in the photometer. The absorption at a wave length of 600 nm is thereby a measure for the number of existing bacteria cells. If the bacteria lyse the sample solution is getting clear by degrees and the measured absorption decreases in the ideal case down to a value of zero. *Staphylococcus* bacteria were cultivated in BHI medium to an OD600 of about 0.8. The not heat activated cells were harvested and resuspended to an OD600 of about 1 in TBST buffer (20 mM Tris/HCl pH 7.5, 60 mM NaCl, 0.1% Tween, 2 mM $CaCl_2$). 990 µl cell suspension was tempered each with 10 µl enzyme solution (enzyme concentration in the test 10 µg/ml) and the decrease in absorption at 600 nm at 30° C. was monitored.

It was found, that a complete lysis of the staphylococci was occurred in non-digested PlyPitti26 and in the plasmin control after about 1000 s, whereas no visual cell lysis has taken place anymore in the samples digested with thrombin or V8 protease, the cell wall lysing enzyme was inactivated completely. The results are shown in FIG. 2B.

EXAMPLE 3

Stabilization of CHAP-AmiPitti26-CBDUSA

A synthetically produced endolysin variant active against staphylococci, which consists of the enzymatically active domains CHAP and Ami of the endolysins of PlyPitti26 and of the cell wall binding domain (CBD) of the endolysin of the prophage Φ SA2USA deriving from the genome of the MRSA strain USA300 (Diep et al., The Lancet, 2006, 367, 731-739; database accession number NC_007793) is described as CHAP-AmiPitti26-CBDUSA.

To stabilize this protein against thrombin digest and digest by V8 protease, both the thrombin cleavage site and V8 cleavage sites lying in the linker between the CHAP— and amidase domains were modified by amino acid substitutions by means of site-directed mutagenesis. The single, double, triple and quadruple mutations performed for that purpose are summarized in table 3. For all mutations given in table 3, endolysin activity against staphylococci was still detected in the plate lysis test, as described below after mutation. The amino acid positions given in the table refer to the respective positions of the wild type sequence and the positions in modified polypeptides respectively, in which no amino acid residues were added. For example the position E163 is in one embodiment of a polypeptide according to the invention with one amino acid addition at position two E164, then the position E167 is E168. In case of more than one amino acid addition the position shifts respectively. If an amino acid residue is introduced only at position 174, the position E163 remains equal, but the position E189 changes to E190.

TABLE 3

| Mutant | Cleavage site V8: V8 protease T: thrombin | substitution |
|---|---|---|
| 1 | E163 (V8) | 163Q |
|   | R167 (T) | 167K |
| 2 | E163 (V8) | 163Q |
|   | R167 (T) | 167A |
| 3 | E163 (V8) | 163A |
|   | R167 (T) | 167K |
| 4 | E163 (V8) | 163A |
|   | R167 (T) | 167A |
| 5 | E179 (V8) | 179Q |
| 6 | E179 (V8) | 179A |
| 7 | E189 (V8) | 189Q |
| 8 | E189 (V8) | 179A |
| 9 | E163 (V8) | 163Q |
|   | R167 (T) | 167A |
|   | E179 (V8) | 179Q |
|   | E189 (V8) | 189Q |
| 10 | E163 (V8) | 163Q |
|   | R167 (T) | 167A |
|   | E179 (V8) | 179A |
|   | E189 (V8) | 189Q |
| 11 | E163 (V8) | 163A |
|   | R167 (T) | 167A |
|   | E179 (V8) | 179Q |
|   | E189 (V8) | 189Q |
| 12 | E163 (V8) | 163A |
|   | R167 (T) | 167A |
|   | E179 (V8) | 179A |
|   | E189 (V8) | 189Q |
| 13 | R167 (T) | 167A |
| 14 | E163 (V8) | 163A |
| 15 | E163 (V8) | 163Q |
| 16 | R167 (T) | 167K |
| 17 | E179 (V8) | 179A |
|   | E189 (V8) | 189Q |

TABLE 3-continued

| Mutant | Cleavage site V8: V8 protease T: thrombin | substitution |
|---|---|---|
| 18 | E179 (V8) | 179Q |
|   | E189 (V8) | 189Q |
| 19 | E163 (V8) | 163Q |
|   | R167 (T) | 167A |
|   | E189 (V8) | 189Q |
| 20 | E163 (V8) | 163A |
|   | R167 (T) | 167A |
|   | E189 (V8) | 189Q |

The endolysins were applied in a concentration of 1 mg/ml into the digest. For the thrombin digest 90 µl protein and 10 µl human thrombin (stock solution with 50 µg/ml) were applied. The samples were incubated over night at 25° C. in buffer (20 mM Tris/HCl pH 7.5, 10 mM DTE, 0.1 mM $ZnSO_4$). A part of the samples were tempered with SDS gel application buffer and were analysed after boiling on SDS polyacrylamide gels. The mutation of R at position 167 against A leads to a complete insensitization against thrombin. The same was true for the mutation of R at position 168 against A, after addition of A at amino acid position two (CHAP-Ami_Pitti26-CBD-USA-Add2).

Non-modified CHAP-Ami_Pitti26-CBD-USA, CHAP-Ami_Pitti26-CBD-USA-Add2 and the respective mutant 4 (E163A, R167A and E164A, R1678 respectively) were also digested with V8 protease. The endolysins were applied in a concentration of 1 mg/ml in the digest. For the V8 protease digest 99 µl protein and 1 µl V8 protease (stock solution with 500 µg/ml) were applied. The samples were incubated for 15 min and 60 min respectively in 20 mM Tris/HCl pH 7.5, 10 mM DTE, 0.1 mM $ZnSO_4$ buffer. A part of the samples were tempered with SDS gel application buffer and were analysed after boiling on SDS polyacrylamide gels. Although, the mutation of E at position 163 and 164 respectively against A does not lead to a complete insensitization against V8 protease, but the mutant of the invention is considerably stabilized, compared to the wild type, in which a complete digest occurs. The modified thrombin cleavage site at position 167/168 plays no role in the performed V8 protease digest. In the modified polypeptides two fragments of about 40 kDa are still available both after 15 min and also after 60 min, which are after 15 min only weak and after 60 min no longer available in the non modified polypeptides.

EXAMPLE 4

Lysis Test with Protease Sensitive and Protease Resistant Endolysins

To investigate, if the polypeptides of the invention already have the desired activity after the amino acid substitution, they were tested in a plate lysis test with different *Staphylococcus* strains. The bacteria strains were cultivated over night in 5 ml cultures in BHI medium and the bacteria cells were centrifuged for 5 min at 4000 UpM in a table centrifuge. The cell pellet was resuspended afterwards in 200 µl PBS buffer (10 mM sodium phosphate, 144 mM NaCl, 50 mM KCl, pH 7.4) and the cells were heat inactivated for 30 min at 80° C. The heat inactivated cells were poured with 15 ml top agar in petri dishes and dried. Then each 5 µg protein was spotted and the agar plates were incubated for 1 h at 30° C. Occurring cell lysis area at the positions of the proteins spotted proteins were evaluated visually and valued depending on size with +++, ++, and + or with −, if no lysis occurred.

The test result for several polypeptides of the invention is summarized in table 4.

| Staphylococcus species | PlyPitti26 (non-modified) | Mutant 10 from table 3 (E163Q, R167A, E179A, E189Q) | Mutant 4 from table 3 (E163A, R167A) | CHAP-AmiPitti26-CBDUSA (non-modified) |
|---|---|---|---|---|
| Staphylococcus aureus MRSA | +++ | +++ | +++ | +++ |
| Staphylococcus aureus MRSA | +++ | +++ | +++ | +++ |
| Staphylococcus aureus MRSA | ++ | +++ | +++ | +++ |
| Staphylococcus epidermis | +++ | +++ | +++ | +++ |
| Staphylococcus equorum | + | ++ | ++ | ++ |
| Staphylococcus sciuri | − | ++ | + | ++ |
| Staphylococcus saprophyticus | − | +++ | ++ | +++ |
| Staphylococcus sciuri | − | − | − | − |
| Staphylococcus aureus MRSA | +++ | +++ | +++ | +++ |
| Staphylococcus epidermidis | +++ | +++ | +++ | +++ |
| Staphylococcus epidermidis koagulase-negative | ++ | ++ | ++ | ++ |
| Staphylococcus haemolyticus koagulase-negative | ++ | ++ | ++ | ++ |
| Staphylococcus epidermidis koagulase-negative | +++ | +++ | +++ | +++ |

Both the non-modified PlyPitti26 and also CHAP-AmiPitti26-CBDUSA had a broad lysis spectrum towards different Staphylococcus strains, wherein the CHAP-AmiPitti26-CBDUSA showed a slightly better lysis activity. The modified polypeptides of the invention mutant 4 and mutant 10 both shown in the table with the amino acid substitutions at the thrombin and different V8 protease cleavage sites respectively had a practically identical activity as the non-modified protein CHAP-AmiPitti26-CBDUSA. This showed that the mutations of the invention did not negatively influence the activity of the cell wall lysing enzymes. The same was true for non-modified CHAP-Ami_Pitti26-CBD-USA-Add2 as well as the respective modified CHAP-Ami_Pitti26-CBD-USA-Add2 polypeptides.

EXAMPLE 5

Modified Cell Wall Binding Enzymes Against *Clostridium difficile*

Two endolysins from different *Cl. difficile* phages (accession numbers YP_529586 for the endolysin from the phage Φ CD119 and YP_001087453 for the endolysin from the strain *Cl. difficile* 630) had a singular caspase 1 cleavage site after amino acid D214, whereas a singular thrombin cleavage site only in endolysin from the phage Φ CD119 at position 87 occurred. Because of the high sequence similarity of both endolysins, besides the modifications of the caspase 1 cleavage sites from D214 to E214, R at position 87 in Φ CD119 endolysin was substituted with K, which was present in the homologous endolysin from the strain *Cl. difficile* 630 at this position and is not recognized by thrombin as cleavage site. Further modifications of the invention are presented in table 2.

EXAMPLE 6

Determination of Protease Sensitive Regions within the Ply511 Sequence

Ply511 has 6 potential cleavage sites for *Staphylococcus* peptidase I (6 glutamates) because of its amino acid sequence. To find out, which regions of the endolysins Ply511 are especially protease sensitive, protease digest experiments were performed with *staphylococcus* peptidase I. For the *staphylococcus* peptidase I degradation 99 µl protein solution (concentration about 1 mg/ml) and 1 µl protease solution (concentration about 0.5 mg/ml) were applied. The samples were incubated for different time intervals (minutes up to several hours) at 37° C. in a buffer with 20 mM Tris/HCl, 100 mM NaCl, pH 8.0. The protein bands were separated on SDS gels. The occurring degradation fragments were blotted on PVDF membranes (polyvinylidenfluoride), well separable bands were cut and N-terminal sequenced. There were three preferred cleavage sites for *staphylococcus* peptidase I after the amino acids E7, E40 and E89.

EXAMPLE 7

Removal of *Staphylococcus* Peptidase I Cleavage Sites in Ply511

At the positions E7, E40 and E89 substitutions were performed either as single substitution or in combination, so that in the occurring mutants other amino acids except glutamate substitute the respective positions, which are no longer cleaved by *staphylococcus* peptidase I. The mutants thus obtained were applied in the protease digest described in example 6 and were afterwards analysed on SDS gels, whether the respective degradation bands still occurred or not. The mutations E7A and E7Q as well as E40A and E40Q turned out as being particularly suitable.

EXAMPLE 8

Resistance to Thrombin and V8 Protease of Different Endolysin Variants of PlyPitti26 and CHAP-AmiPitti26-CBDUSA Different mutation combinations of the invention from table 3 were introduced into the Plypitti26 variant CHAP-AmiPitti26-CBDUSA and CHAP-AmiPitti26-CBDUSA-Add2 and partially combined with further mutations. Afterwards these endolysin variants were tested for their resistance to thrombin and V8 protease as well as the enzyme activity (detection as described in example 3). The results are summarized in table 5 for CHAP-AmiPitti26-CBDUSA and the modifications thereof. The results for CHAP-AmiPitti26-CBDUSA-Add2 and the modifications thereof (amino acid positions are each shifted by one position in the direction to the C-terminus towards the positions in the table) are identical and not described again in table 5.

TABLE 5

Resistance to thrombin und V8 protease of different mutants of CHAP-Amipitti26_CBDUSA
(described as EADpitti26_CBDUSA in the table) in comparison to Plypitti26-wild type

| Property | Assay | plypitti26 | EADpitti26_CBDUSA | EADpitti26_CBDUSA | EADpitti26_CBDUSA | EADpitti26_CBDUSA | EADpitti26_CBDUSA | EADpitti26_CBDUSA | EADpitti26_CBDUSA |
|---|---|---|---|---|---|---|---|---|---|
| | | | | | Mutations | | | | |
| | | | E163A, R167A, Y200H | E163A, R167A, E179A, E189Q, Y200H | L55H, L56T, E163A, R167A, Y200H | L55H, L56T, E163A, R167A, E179A, E189Q, Y200H | L55H, L56T, | E163A, R167A | |
| Thrombin resistance | SDS-PAGE | — | +++ | ++ | +++ | +++ | — | +++ | + |
| Thrombin resistance | liquid lysis | — | — | — | ++ | ++ | — | — | + |
| V8 protease resistance | SDS-PAGE | — | — | + | — | + | — | — | — |

It was shown that the endolysin variants of the invention CHAP-Amipitti26_CBDUSA (E163A, R167A, Y200H), CHAP-Amipitti26_CBDUSA (E163A, R167A, E179A, E189Q, Y200H), CHAP-Amipitti26_CBDUSA (L55H, L56T, E163A, R167A, Y200H), CHAP-Amipitti26_CBDUSA (L55H, L56T, E163A, R167A, E179A, E189Q, Y200H) and CHAP-Amipitti26_CBDUSA (E163A, R167A) as well as CHAP-Amipitti26_CBDUSA-Add2 (E164A, R168A, Y201H), CHAP-Amipitti26_CBDUSA-Add2 (E164A, R168A, E180A, E190Q, Y201H), CHAP-Amipitti26_CBDUSA-Add2 (L56H, L57T, E164A, R168A, Y201H), CHAP-Amipitti26_CBDUSA-Add2 (L56H, L57T, E164A, R168A, E180A, E190Q, Y201H) and CHAP-Amipitti26_CBDUSA-Add2 (E164A, R168A) had a good to very good resistance to thrombin digest. The endolysin variants CHAP-Amipitti26_CBDUSA (L55H, L56T, E163A, R167A, Y200H) and CHAP-Amipitti26_CBDUSA (L55H, L56T, E163A, R167A, E179A, E189Q, Y200H) as well as CHAP-Amipitti26_CBDUSA-Add2 (L56H, L57T, E164A, R168A, Y201H) and CHAP-Amipitti26_CBDUSA-Add2 (L56H, L57T, E164A, R168A, E180A, E190Q, Y201H) also showed a high enzyme activity in the liquid lysis test after thrombin digest. The endolysin variants CHAP-Amipitti26_CBDUSA (E163A, R167A, E179A, E189Q, Y200H) and CHAP-Amipitti26_CBDUSA (L55H, L56T, E163A, R167A, E179A, E189Q, Y200H), as well as CHAP-Amipitti26_CBDUSA-Add2 (E164A, R168A, E180A, E190Q, Y201H) and CHAP-Amipitti26_CBDUSA-Add2 (L56H, L57T, E164A, R168A, E180A, E190Q, Y201H) had an improved resistance to V8 protease digest. Particularly the substitutions E179A and E189Q and E180A and E190Q, respectively proved beneficial here.

EXAMPLE 9

Endolysins with Protease Cleavage Sites According to the Invention

Whether a substitution of an amino acid residue proves beneficial, may be detected with the detection for protease stability and endolysin activity as described above. A series of examples for endolysins, which lyse members from different genera of bacteria and which could be stabilized according to the invention against protease degradation, are shown in table 6. The protease cleavage sites were determined with the program PeptideCutter (Gasteiger et al., Protein Identification and Analysis Tools on the ExPASy Server in John M. Walker (ed): John M. Walker (ed): The Proteomics Protocols Handbook, Humana Press (2005)).

TABLE 6

Endolysins with protease cleavage sites of table 1 Protease cleavage sites for

| Endolysin (lysis of bacteria of the genera) | Source for the amino acid sequence (NCBI accession number) | Thrombin; number of amino acid P1 and recognition sequence | Caspase1; number of amino acid P1 and recognition sequence | Clostripain; number | V8 Protease; number |
|---|---|---|---|---|---|
| PlyPitti26 (Staphylococcus) | New | 167 (TAPR) | | 20 | 24 |
| CHAP-AmiPitti26-CBDUSA (Staphylococcus) | New | 167 (TAPR) | | 21 | 23 |

TABLE 6-continued

Endolysins with protease cleavage sites of table 1 Protease cleavage sites for

| Endolysin (lysis of bacteria of the genera) | Source for the amino acid sequence (NCBI accession number) | Thrombin; number of amino acid P1 and recognition sequence | Caspase1; number of amino acid P1 and recognition sequence | Clostripain; number | V8 Protease; number |
|---|---|---|---|---|---|
| Amidase of Staphylococcus phage SAP-2 | (YP_0014915 39) | | 42 (YITDG) | 7 | 9 |
| E1 Endolysin (Enterococcus) | (NP_814147) | 106 (FLPR) | 358 (YGTDY) | 6 | 15 |
| E2 Endolysin (Enterococcus) | (NP_815016) | | 330 (YIADG) and Caspase 10 31 (IEAD) | 13 | 13 |
| E5 Endolysin (Enterococcus) | (NP_815749) | | 147 (WLADY) | 8 | 13 |
| Fab25 (Enterococus) | Neu | | 112 (LLHDL) | 14 | 9 |
| B30-PlyGBS (Streptococcus) | (AAR99416) | | 388 (LSTDY) | 12 | 18 |
| Palamidase (Streptococcus) | (CAB07986) | | | 14 | 13 |
| Cpl Lysin (Streptococcus) | (2IU_A) | | 133 (FTHDN) | 7 | 12 |
| LysK (Staphylococcus) | (YP_024461) | | 60 (LITDY) and 67 (WLTDN) | 16 | 18 |
| Ply187 (Staphylococcus) | (CAA69022) | | 596 (YATDI) | 23 | 20 |
| Lysostaphin (Staphylococcus) | (AAB53783) | | | 9 | 51 |
| Ply511 (Listeria) | (Q38653) | | | 6 | 6 |
| Ply118 (Listeria) | EP0781349 B1; SEQ ID NO: 4 | 262 (GTPR) | 129 (YGTDT) | 8 | 6 |
| PlyA500 (Listeria) | (AAY528 12) | | | 12 | 12 |
| Ply21 (Bacillus) | (CAA72267) | 82 (GRG) | | 15 | 13 |
| PlyBA (Bacillus) | (CAA72266) | | | 11 | 25 |
| Ply12 (Bacillus) | (CAA72264) | | | 14 | 10 |
| PlyCD119 (Clostridium) | New | 87 (GRG) | 214 (LVTDI) | 7 | 13 |
| Ply3626 (Clostridium) | US 7,371,375 B2; SEQ ID NO: 2 | | | 17 | 27 |

EXAMPLE 10

Determination of Clostripain Cleavage Sites in Listeria Endolysins

As can be seen from table 6, potential cleavage sites for clostripain in endolysins are often present in higher number (6 to 23 in the described examples). Since a substitution of all potential cleavage sites may influence negatively the activity of the endolysin, it is useful to determine the cleavage sites available for the proteases and to modify only such. The listeria endolysin Ply511 contains six potential cleavage sites for clostripain. It was performed a clostripain digest of Ply511, to determine the sensitive regions for clostripain of the endolysin. Ply511 (0.1 mg/ml) was digested for 3 h and over night respectively at room temperature with 5 units clostripain (unit definition according to manufacture's data, Sigma) in 60 µl sample volume with the following composition: 25 mM sodium phosphate, 1 mM calcium acetate, 2.5 mM DTT, pH 7.6. The occurring protein fragments were separated by SDS gel electrophoresis (gradient gel 10-20% acryl amide). Three bands occurred (molecular weights about 25 kDa, about 14 kDa, about 10 kDa), which were blotted on PVDF membranes, afterwards they were cut and sequenced N-terminal via Edman-degradation.

There were the following N-terminal sequences for the fragments:
1. (M) V K Y T V E N K; the N-terminal methionine was partly cleaved
2. DKLAK
3. TSNATTF This result shows, that from the six potential clostripain cleavage sites (R46, R62, R92, R221, R312, R326) two are recognized by the protease, namely R92 and R221. Stabilized variants of Ply511 according to the invention have at these positions substitutions from R to other amino acid residues, in particular R62K or R62A as well as, R221K or R221A.

EXAMPLE 11

Protease Degradation of a Therapeutically Applicable Protein in Different Organs and Determination of the Protease Sensitive Regions In pharmacokinetic studies it was found out, that the endolysin CHAP-Amipitti26_CBDUSA-Add2 (L56H, L57T, E164A, R168A, Y201H) used against staphylococci was no longer detectable at different speeds in different organs. To test, whether this is attributed to protease degradation, the endolysin was incubated with organ extracts and potential degradation bands were analysed. Tissue samples from liver, heart, spleen, kidney and lungs of rats were deep-frozen, were again thawed and homogenized in the same volume PBS buffer. Per sample 40 µl CHAP-Amipitti26_CBDUSA-Add2 (L56H, L57T, E164A, R168A, Y201H) (1 mg/ml in 20 mM Tris, pH 8.0) and 10 µl organ extract (1:20 diluted with PBS) were mixed and incubated for 18 h at room temperature and at 4° C. respectively. In the protein controls instead of organ extract only PBS buffer was added and incubated for the same time as well as one protein control was prepared without incubation time. As further controls each organ extract without addition of endolysin was analysed. The samples were mixed with sample buffer and applied on 12% SDS gels.

It was shown, that only in the samples, to which kidney extract was added, a significant protein degradation took place during the experimental period, in all other organ extracts as well as the controls the endolysin remains stable. By incubation with the kidney extract larger protein fragments with defined size occurred, so that it was likely, that the endolysin was degraded by one or a few kidney specific proteases. To determine the sensitive region for this/these protease(s) the occurring bands (marked with arrows and the numbers 1 to 7) were blotted on a PVDF membrane and the polypeptides were N-terminally sequenced by Edman-degradation. The approximate size of the occurring fragments was derived by means of a standard curve, which was created from the running distances of the bands of the molecular weight standard, from which the molecular weight was known. The following fragments occurred, which are summarized in table 7. The occurring protein sections were determined starting from the determined N-terminal sequences in combination with the fragment sizes.

TABLE 7

Fragments of endolysin CHAP-Amipitti26_CBDUSA-Add2 (L56H, L57T, E164A, R168A, Y201H) after degradation by kidney specific protease(s)

| Band no. | size (calculated from the running distance in the gel) kDa | N-terminal sequence | protein sector | size (calculated from the amino acid sequence) kDa |
| --- | --- | --- | --- | --- |
| 1 | 58 | ASIIMEV | complete protein, N-terminal M cleaved | 55 |
| 2 | 43 | ASIIM | N-terminal fragment, CHAP- and amidase domain, complete BAD to the cleavage site before band 5 (ASSNTV) | 44 |
| 3 | 25 | ASKKETAPQ | Amidase domain, to the cleavage site before band 5 (ASSNTV). | 24 |
| 4 | 19 | ASIIMEVATMQ | N-terminal fragment, CHAP-19 domain to the cleavage site before band 3 (ASKKETAPQ). | |
| 5 | 15 | ASSNTV | C-terminal fragment, CBD. | 12 |
| 6 | 20 | ASIIMEVAT | N-terminal fragment, CHAP-domain to the cleavage site before band 7 (XPTQA). | 20 |
| 7 | 41 | XPTQA | C-terminal fragment, amidase domain and CBD. | 36 |

X: amino acid, which could not have been defined.

From the determination of the N-terminal sequences in combination with the size determination of the occurring fragments it resulted that the proteases present in the kidney extract cleave the endolysin CHAP-Amipitti26_CBDUSA-Add2 at 3 positions, namely after the amino acids Q171, Q175 and S384. A search for conservative domains within the endolysins CHAP-Amipitti26_CBDUSA-Add2 in the CDD (conserved domain database) resulted in 3 conserved domains, namely N-terminal a CHAP-domain (amino acids 28 to 158), followed by an amidase_2 domain (amino acids 199 to 346) as well as a C-terminally occurring SH3_5 domain (amino acids 413 to 478). The CHAP— and amidase 2 domain are the EADs, as the SH35 domain forms the CBD. Between the CHAP and amidase 2 domain occurs a domain linker (amino acids 159 to 198), as well as a second linker between the amidase 2 domain and the CBD (amino acids 347 to 412). All three found cleavage sites occurred in the middle of the domain linker regions, which proved less stable than the conserved domains. The proteases from the kidney, which were responsible for the degradation, could not be identified, but it struck, that at least one protease requires a Q at position P1 as well as that all three protease recognition sites were rich in serines and alanines.

The invention claimed is:

1. An isolated polypeptide comprising the sequence selected from the group consisting of SEQ ID NO: 1, SEQ ID NO: 2, SEQ ID NO: 3, SEQ ID NO: 11, SEQ ID NO: 12 and SEQ ID NO: 13.

2. A pharmaceutical composition comprising a isolated polypeptide comprising the sequence selected from the group consisting of SEQ ID NO: 1, SEQ ID NO: 2, SEQ ID NO: 3, SEQ ID NO: 11, SEQ ID NO: 12 and SEQ ID NO: 13.

3. A method of inhibiting the growth of Gram-positive bacterium comprising contacting said bacterium with a polypeptide comprising the sequence selected from the group consisting of SEQ ID NO: 1, SEQ ID NO: 2, SEQ ID NO: 3, SEQ ID NO: 11, SEQ ID NO: 12 and SEQ ID NO: 13.

4. The method of claim 3, wherein said Gram-positive bacteria are selected from the group consisting of clostridia, bacilli, *listeria*, staphylococci, lactobacilli, enterococci, aerococci, pediococci, streptococci, mycoplasmas, *leuconostoc*, or a combination thereof.

* * * * *

UNITED STATES PATENT AND TRADEMARK OFFICE
CERTIFICATE OF CORRECTION

| | | |
|---|---|---|
| PATENT NO. | : 8,492,519 B2 | Page 1 of 1 |
| APPLICATION NO. | : 12/674369 | |
| DATED | : July 23, 2013 | |
| INVENTOR(S) | : Grallert et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 528 days.

Signed and Sealed this
Third Day of February, 2015

Michelle K. Lee
*Deputy Director of the United States Patent and Trademark Office*

SEQUENCE LISTING

<160> NUMBER OF SEQ ID NOS: 24

<210> SEQ ID NO 1
<211> LENGTH: 496
<212> TYPE: PRT
<213> ORGANISM: Artificial
<220> FEATURE:
<223> OTHER INFORMATION: Synthetic peptide

<400> SEQUENCE: 1

```
Met Ser Ile Ile Met Glu Val Ala Thr Met Gln Ala Lys Leu Thr Lys
1               5                   10                  15

Lys Glu Phe Ile Glu Trp Leu Lys Thr Ser Glu Gly Lys Gln Phe Asn
            20                  25                  30

Val Asp Leu Trp Tyr Gly Phe Gln Cys Phe Asp Tyr Ala Asn Ala Gly
        35                  40                  45

Trp Lys Val Leu Phe Gly Leu Leu Lys Gly Leu Gly Ala Lys Asp
    50                  55                  60

Ile Pro Phe Ala Asn Asn Phe Asp Gly Leu Ala Thr Val Tyr Gln Asn
65                  70                  75                  80

Thr Pro Asp Phe Leu Ala Gln Pro Gly Asp Met Val Val Phe Gly Ser
                85                  90                  95

Asn Tyr Gly Ala Gly Tyr Gly His Val Ala Trp Val Ile Glu Ala Thr
            100                 105                 110

Leu Asp Tyr Ile Ile Val Tyr Glu Gln Asn Trp Leu Gly Gly Gly Trp
        115                 120                 125

Thr Asp Arg Ile Glu Gln Pro Gly Trp Gly Trp Glu Lys Val Thr Arg
    130                 135                 140

Arg Gln His Ala Tyr Asp Phe Pro Met Trp Phe Ile Arg Pro Asn Phe
145                 150                 155                 160

Lys Ser Glu Thr Ala Pro Ala Ser Ile Gln Ser Pro Thr Gln Ala Ser
                165                 170                 175

Lys Lys Glu Thr Ala Lys Pro Gln Pro Lys Ala Val Glu Leu Lys Ile
            180                 185                 190

Ile Lys Asp Val Val Lys Gly Tyr Asp Leu Pro Lys Arg Gly Gly Asn
        195                 200                 205

Pro Lys Gly Ile Val Ile His Asn Asp Ala Gly Ser Lys Gly Ala Thr
    210                 215                 220

Ala Glu Ala Tyr Arg Asn Gly Leu Val Asn Ala Pro Ser Ser Arg Leu
225                 230                 235                 240

Glu Ala Gly Ile Ala His Ser Tyr Val Ser Gly Asn Thr Val Trp Gln
                245                 250                 255

Ala Leu Asp Glu Ser Gln Val Gly Trp His Thr Ala Asn Gln Leu Gly
            260                 265                 270
```

-continued

```
Asn Lys Tyr Tyr Tyr Gly Ile Glu Val Cys Gln Ser Met Gly Ala Asp
        275                 280                 285

Asn Ala Thr Phe Leu Lys Asn Glu Gln Ala Thr Phe Gln Glu Cys Ala
        290                 295                 300

Arg Leu Leu Lys Lys Trp Gly Leu Pro Ala Asn Arg Asn Thr Ile Arg
305                 310                 315                 320

Leu His Asn Glu Phe Thr Ser Thr Ser Cys Pro His Arg Ser Ser Val
            325                 330                 335

Leu His Thr Gly Phe Asp Pro Val Thr Arg Gly Leu Leu Pro Glu Asp
                340                 345                 350

Lys Arg Leu Gln Leu Lys Asp Tyr Phe Ile Lys Gln Ile Arg Ala Tyr
            355                 360                 365

Met Asp Gly Lys Ile Pro Val Ala Thr Val Ser Asn Glu Ser Ser Ala
    370                 375                 380

Ser Ser Asn Thr Val Lys Pro Val Ala Glu Leu Met Pro Pro Val Pro
385                 390                 395                 400

Ala Gly Tyr Thr Leu Asp Lys Asn Asn Val Pro Tyr Lys Lys Glu Gln
                405                 410                 415

Gly Asn Tyr Thr Val Ala Asn Val Lys Gly Asn Asn Val Arg Asp Gly
            420                 425                 430

Tyr Ser Thr Asn Ser Arg Ile Thr Gly Val Leu Pro Asn Asn Thr Thr
        435                 440                 445

Ile Thr Tyr Asp Gly Ala Tyr Cys Ile Asn Gly Tyr Arg Trp Ile Thr
    450                 455                 460

Tyr Ile Ala Asn Ser Gly Gln Arg Arg Tyr Ile Ala Thr Gly Glu Val
465                 470                 475                 480

Asp Ile Ala Gly Asn Arg Ile Ser Ser Phe Gly Lys Phe Ser Ala Val
                485                 490                 495

<210> SEQ ID NO 2
<211> LENGTH: 496
<212> TYPE: PRT
<213> ORGANISM: Artificial
<220> FEATURE:
<223> OTHER INFORMATION: Synthetic peptide

<400> SEQUENCE: 2

Met Ser Ile Ile Met Glu Val Ala Thr Met Gln Ala Lys Leu Thr Lys
1               5                   10                  15

Lys Glu Phe Ile Glu Trp Leu Lys Thr Ser Gly Lys Gln Phe Asn
            20                  25                  30

Val Asp Leu Trp Tyr Gly Phe Gln Cys Phe Asp Tyr Ala Asn Ala Gly
        35                  40                  45

Trp Lys Val Leu Phe Gly Leu Leu Lys Gly Leu Gly Ala Lys Asp
    50                  55                  60

Ile Pro Phe Ala Asn Asn Phe Asp Gly Leu Ala Thr Val Tyr Gln Asn
65                  70                  75                  80

Thr Pro Asp Phe Leu Ala Gln Pro Gly Asp Met Val Val Phe Gly Ser
                85                  90                  95

Asn Tyr Gly Ala Gly Tyr Gly His Val Ala Trp Val Ile Glu Ala Thr
            100                 105                 110

Leu Asp Tyr Ile Ile Val Tyr Glu Gln Asn Trp Leu Gly Gly Gly Trp
        115                 120                 125

Thr Asp Arg Ile Glu Gln Pro Gly Trp Gly Trp Glu Lys Val Thr Arg
    130                 135                 140
```

Arg Gln His Ala Tyr Asp Phe Pro Met Trp Phe Ile Arg Pro Asn Phe
145                 150                 155                 160

Lys Ser Ala Thr Ala Pro Ala Ser Ile Gln Ser Pro Thr Gln Ala Ser
            165                 170                 175

Lys Lys Glu Thr Ala Lys Pro Gln Pro Lys Ala Val Glu Leu Lys Ile
            180                 185                 190

Ile Lys Asp Val Val Lys Gly Tyr Asp Leu Pro Lys Arg Gly Gly Asn
            195                 200                 205

Pro Lys Gly Ile Val Ile His Asn Asp Ala Gly Ser Lys Gly Ala Thr
210                 215                 220

Ala Glu Ala Tyr Arg Asn Gly Leu Val Asn Ala Pro Ser Ser Arg Leu
225                 230                 235                 240

Glu Ala Gly Ile Ala His Ser Tyr Val Ser Gly Asn Thr Val Trp Gln
                245                 250                 255

Ala Leu Asp Glu Ser Gln Val Gly Trp His Thr Ala Asn Gln Leu Gly
            260                 265                 270

Asn Lys Tyr Tyr Tyr Gly Ile Glu Val Cys Gln Ser Met Gly Ala Asp
            275                 280                 285

Asn Ala Thr Phe Leu Lys Asn Glu Gln Ala Thr Phe Gln Glu Cys Ala
290                 295                 300

Arg Leu Leu Lys Lys Trp Gly Leu Pro Ala Asn Arg Asn Thr Ile Arg
305                 310                 315                 320

Leu His Asn Glu Phe Thr Ser Thr Ser Cys Pro His Arg Ser Ser Val
                325                 330                 335

Leu His Thr Gly Phe Asp Pro Val Thr Arg Gly Leu Leu Pro Glu Asp
            340                 345                 350

Lys Arg Leu Gln Leu Lys Asp Tyr Phe Ile Lys Gln Ile Arg Ala Tyr
            355                 360                 365

Met Asp Gly Lys Ile Pro Val Ala Thr Val Ser Asn Glu Ser Ser Ala
370                 375                 380

Ser Ser Asn Thr Val Lys Pro Val Ala Glu Leu Met Pro Pro Val Pro
385                 390                 395                 400

Ala Gly Tyr Thr Leu Asp Lys Asn Asn Val Pro Tyr Lys Lys Glu Gln
                405                 410                 415

Gly Asn Tyr Thr Val Ala Asn Val Lys Gly Asn Asn Val Arg Asp Gly
            420                 425                 430

Tyr Ser Thr Asn Ser Arg Ile Thr Gly Val Leu Pro Asn Asn Thr Thr
            435                 440                 445

Ile Thr Tyr Asp Gly Ala Tyr Cys Ile Asn Gly Tyr Arg Trp Ile Thr
            450                 455                 460

Tyr Ile Ala Asn Ser Gly Gln Arg Arg Tyr Ile Ala Thr Gly Glu Val
465                 470                 475                 480

Asp Ile Ala Gly Asn Arg Ile Ser Ser Phe Gly Lys Phe Ser Ala Val
            485                 490                 495

<210> SEQ ID NO 3
<211> LENGTH: 496
<212> TYPE: PRT
<213> ORGANISM: Artificial
<220> FEATURE:
<223> OTHER INFORMATION: Synthetic peptide -continued

```
<400> SEQUENCE: 3

Met Ser Ile Ile Met Glu Val Ala Thr Met Gln Ala Lys Leu Thr Lys
1               5                   10                  15

Lys Glu Phe Ile Glu Trp Leu Lys Thr Ser Glu Gly Lys Gln Phe Asn
                20                  25                  30

Val Asp Leu Trp Tyr Gly Phe Gln Cys Phe Asp Tyr Ala Asn Ala Gly
            35                  40                  45

Trp Lys Val Leu Phe Gly Leu Leu Lys Gly Leu Ala Lys Asp
        50                  55                  60

Ile Pro Phe Ala Asn Asn Phe Asp Gly Leu Ala Thr Val Tyr Gln Asn
65                  70                  75                  80

Thr Pro Asp Phe Leu Ala Gln Pro Gly Asp Met Val Val Phe Gly Ser
                85                  90                  95

Asn Tyr Gly Ala Gly Tyr Gly His Val Ala Trp Val Ile Glu Ala Thr
            100                 105                 110

Leu Asp Tyr Ile Ile Val Tyr Glu Gln Asn Trp Leu Gly Gly Gly Trp
        115                 120                 125

Thr Asp Arg Ile Glu Gln Pro Gly Trp Gly Trp Glu Lys Val Thr Arg
    130                 135                 140

Arg Gln His Ala Tyr Asp Phe Pro Met Trp Phe Ile Arg Pro Asn Phe
145                 150                 155                 160

Lys Ser Gln Thr Ala Pro Ala Ser Ile Gln Ser Pro Thr Gln Ala Ser
                165                 170                 175

Lys Lys Ala Thr Ala Lys Pro Gln Pro Lys Ala Val Gln Leu Lys Ile
            180                 185                 190

Ile Lys Asp Val Val Lys Gly Tyr Asp Leu Pro Lys Arg Gly Gly Asn
        195                 200                 205

Pro Lys Gly Ile Val Ile His Asn Asp Ala Gly Ser Lys Gly Ala Thr
    210                 215                 220

Ala Glu Ala Tyr Arg Asn Gly Leu Val Asn Ala Pro Ser Ser Arg Leu
225                 230                 235                 240

Glu Ala Gly Ile Ala His Ser Tyr Val Ser Gly Asn Thr Val Trp Gln
                245                 250                 255

Ala Leu Asp Glu Ser Gln Val Gly Trp His Thr Ala Asn Gln Leu Gly
            260                 265                 270

Asn Lys Tyr Tyr Tyr Gly Ile Glu Val Cys Gln Ser Met Gly Ala Asp
        275                 280                 285

Asn Ala Thr Phe Leu Lys Asn Glu Gln Ala Thr Phe Gln Glu Cys Ala
    290                 295                 300

Arg Leu Leu Lys Lys Trp Gly Leu Pro Ala Asn Arg Asn Thr Ile Arg
305                 310                 315                 320

Leu His Asn Glu Phe Thr Ser Thr Ser Cys Pro His Arg Ser Ser Val
                325                 330                 335

Leu His Thr Gly Phe Asp Pro Val Thr Arg Gly Leu Leu Pro Glu Asp
            340                 345                 350

Lys Arg Leu Gln Leu Lys Asp Tyr Phe Ile Lys Gln Ile Arg Ala Tyr
        355                 360                 365

Met Asp Gly Lys Ile Pro Val Ala Thr Val Ser Asn Glu Ser Ser Ala
    370                 375                 380

Ser Ser Asn Thr Val Lys Pro Val Ala Glu Leu Met Pro Pro Val Pro
385                 390                 395                 400
```

```
Ala Gly Tyr Thr Leu Asp Lys Asn Asn Val Pro Tyr Lys Lys Glu Gln
                405                 410                 415

Gly Asn Tyr Thr Val Ala Asn Val Lys Gly Asn Val Arg Asp Gly
            420                 425                 430

Tyr Ser Thr Asn Ser Arg Ile Thr Gly Val Leu Pro Asn Asn Thr Thr
        435                 440                 445

Ile Thr Tyr Asp Gly Ala Tyr Cys Ile Asn Gly Tyr Arg Trp Ile Thr
    450                 455                 460

Tyr Ile Ala Asn Ser Gly Gln Arg Arg Tyr Ile Ala Thr Gly Glu Val
465                 470                 475                 480

Asp Ile Ala Gly Asn Arg Ile Ser Ser Phe Gly Lys Phe Ser Ala Val
                485                 490                 495

<210> SEQ ID NO 4
<211> LENGTH: 271
<212> TYPE: PRT
<213> ORGANISM: Artificial
<220> FEATURE:
<223> OTHER INFORMATION: Synthetic peptide

<400> SEQUENCE: 4

Met Lys Ile Gly Ile Asn Cys Gly His Thr Lys Thr Gly Ala Gly Ser
1               5                   10                  15

Gly Ala Ile Gly Lys Ile Asn Glu Ser Ile Glu Thr Arg Asn Val Gly
            20                  25                  30

Tyr Lys Val Ile Asp Lys Leu Lys Lys Leu Gly Asn Asn Val Val Asp
        35                  40                  45

Cys Thr Ile Asp Lys Ala Ser Thr Gln Ser Glu Cys Leu Ser Lys Ile
    50                  55                  60

Thr Ala Gln Ala Asn Arg Gln Asp Leu Asp Trp Phe Ile Ser Ile His
65                  70                  75                  80

Phe Asn Ala Gly Gly Gly Lys Gly Cys Glu Val Tyr Thr Tyr Lys Gly
                85                  90                  95

Lys Gln Tyr Gln Asp Ala Ile Asp Val Cys Lys Lys Ile Ser Asp Leu
                100                 105                 110

Gly Phe Thr Asn Arg Gly Val Lys Asp Gly Ser Gly Leu Tyr Val Val
            115                 120                 125

Lys Lys Thr Lys Ala Lys Ser Met Leu Ile Glu Val Cys Phe Val Asp
130                 135                 140

Thr Glu Asp Ala Asn Lys Tyr Leu Ser Leu Gly Ala Asp Lys Leu Ala
145                 150                 155                 160

Thr Ala Ile Val Glu Ala Ile Thr Lys His Ile Ser Ser Ala Glu Glu
                165                 170                 175

Asn Asn Tyr Asn Arg Tyr Lys His Thr Ile Val Tyr Ser Gly Asp Asp
            180                 185                 190

Lys Val Ser Ala Asp Ile Leu Gly Leu Tyr Tyr Lys Arg Lys Lys Glu
        195                 200                 205

Ser Tyr Leu Val Thr Glu Ile Lys Asp Tyr Lys Pro His Arg Thr Gln
210                 215                 220

Asn Leu Tyr Val Ile Gly Gly Val Thr Cys Asn Lys Met Lys Glu Met
225                 230                 235                 240

Ser Lys Thr Thr Gly Glu Lys Phe Thr Gln Leu Tyr Gly Asn Asp Val
                245                 250                 255

Trp Ser Thr Met Asp Lys Ala Ile Glu Phe Val Lys Glu Lys Leu
            260                 265                 270
```

```
<210> SEQ ID NO 5
<211> LENGTH: 271
<212> TYPE: PRT
<213> ORGANISM: Artificial
<220> FEATURE:
<223> OTHER INFORMATION: Synthetic peptide

<400> SEQUENCE: 5

Met Lys Ile Gly Val Asn Cys Gly His Thr Lys Thr Gly Ala Gly Ser
1               5                   10                  15

Gly Ala Ile Gly Lys Ile Asn Glu Ser Ile Glu Thr Arg Asn Val Gly
            20                  25                  30

Tyr Lys Val Ile Asp Lys Leu Lys Thr Leu Gly Asn Asn Val Val Asp
        35                  40                  45

Cys Thr Ile Asp Lys Ala Ser Thr Gln Ser Glu Cys Leu Ser Lys Ile
    50                  55                  60

Ala Thr Gln Ala Asn Arg Gln Asp Leu Asp Trp Phe Ile Ser Ile His
65                  70                  75                  80

Phe Asn Ala Gly Lys Gly Lys Gly Cys Glu Val Tyr Thr Tyr Lys Gly
                85                  90                  95

Lys Gln Tyr Gln Asp Ala Ile Asp Val Cys Lys Lys Ile Ser Asp Leu
            100                 105                 110

Gly Phe Thr Asn Arg Gly Val Lys Asp Gly Ser Gly Leu Tyr Val Val
        115                 120                 125

Lys Lys Thr Lys Ala Lys Ser Met Leu Ile Glu Val Cys Phe Val Asp
    130                 135                 140

Ser Glu Asp Ala Asn Lys Tyr Leu Ser Leu Gly Ala Asp Lys Leu Ala
145                 150                 155                 160

Thr Ala Ile Val Glu Ala Ile Thr Lys His Ile Ser Ser Ala Glu Glu
                165                 170                 175

Asn Asn Tyr Asn Arg Tyr Lys His Thr Ile Val Tyr Ser Gly Asp Asp
            180                 185                 190

Lys Val Ser Ala Asp Ile Leu Gly Leu Tyr Tyr Lys Arg Lys Lys Glu
        195                 200                 205

Ser Tyr Leu Val Thr Glu Ile Lys Asp Tyr Lys Pro His Arg Thr Gln
    210                 215                 220

Asn Leu Tyr Val Ile Gly Gly Val Thr Cys Asn Lys Met Lys Glu Met
225                 230                 235                 240

Ser Lys Thr Thr Gly Glu Lys Phe Thr Gln Leu Tyr Gly Asn Asp Val
                245                 250                 255

Trp Ser Thr Met Asp Lys Ala Ile Glu Phe Val Lys Glu Lys Leu
            260                 265                 270

<210> SEQ ID NO 6
<211> LENGTH: 341
<212> TYPE: PRT
<213> ORGANISM: Artificial
<220> FEATURE:
<223> OTHER INFORMATION: Synthetic peptide

<400> SEQUENCE: 6

Met Val Lys Tyr Thr Val Ala Asn Lys Ile Ile Ala Gly Leu Pro Lys
1               5                   10                  15

Gly Lys Leu Lys Gly Ala Asn Phe Val Ile Ala His Glu Thr Ala Asn
            20                  25                  30

Ser Lys Ser Thr Ile Asp Asn Gln Val Ser Tyr Met Thr Arg Asn Trp
        35                  40                  45
```

```
Lys Asn Ala Phe Val Thr His Phe Val Gly Gly Gly Arg Val Val
     50                  55                  60

Gln Val Ala Asn Val Asn Tyr Val Ser Trp Gly Ala Gly Gln Tyr Ala
 65              70                  75                  80

Asn Ser Tyr Ser Tyr Ala Gln Val Glu Leu Cys Arg Thr Ser Asn Ala
             85                  90                  95

Thr Thr Phe Lys Lys Asp Tyr Glu Val Tyr Cys Gln Leu Leu Val Asp
            100                 105                 110

Leu Ala Lys Lys Ala Gly Ile Pro Ile Thr Leu Asp Ser Gly Ser Lys
        115                 120                 125

Thr Ser Asp Lys Gly Ile Lys Ser His Lys Trp Val Ala Asp Lys Leu
    130                 135                 140

Gly Gly Thr Thr His Gln Asp Pro Tyr Ala Tyr Leu Ser Ser Trp Gly
145                 150                 155                 160

Ile Ser Lys Ala Gln Phe Ala Ser Asp Leu Ala Lys Val Ser Gly Gly
                165                 170                 175

Gly Asn Thr Gly Thr Ala Pro Ala Lys Pro Ser Thr Pro Ala Pro Lys
            180                 185                 190

Pro Ser Thr Pro Ser Thr Asn Leu Asp Lys Leu Gly Leu Val Asp Tyr
        195                 200                 205

Met Asn Ala Lys Lys Met Asp Ser Ser Tyr Ser Asn Arg Asp Lys Leu
    210                 215                 220

Ala Lys Gln Tyr Gly Ile Ala Asn Tyr Ser Gly Thr Ala Ser Gln Asn
225                 230                 235                 240

Thr Thr Leu Leu Ser Lys Ile Lys Gly Gly Ala Pro Lys Pro Ser Thr
                245                 250                 255

Pro Ala Pro Lys Pro Ser Thr Ser Thr Ala Lys Lys Ile Tyr Phe Pro
            260                 265                 270

Pro Asn Lys Gly Asn Trp Ser Val Tyr Pro Thr Asn Lys Ala Pro Val
        275                 280                 285

Lys Ala Asn Ala Ile Gly Ala Ile Asn Pro Thr Lys Phe Gly Gly Leu
    290                 295                 300

Thr Tyr Thr Ile Gln Lys Asp Arg Gly Asn Gly Val Tyr Glu Ile Gln
305                 310                 315                 320

Thr Asp Gln Phe Gly Arg Val Gln Val Tyr Gly Ala Pro Ser Thr Gly
                325                 330                 335

Ala Val Ile Lys Lys
            340

<210> SEQ ID NO 7
<211> LENGTH: 341
<212> TYPE: PRT
<213> ORGANISM: artificial
<220> FEATURE:
<223> OTHER INFORMATION: Synthetic peptide

<400> SEQUENCE: 7

Met Val Lys Tyr Thr Val Glu Asn Lys Ile Ile Ala Gly Leu Pro Lys
1               5                   10                  15

Gly Lys Leu Lys Gly Ala Asn Phe Val Ile Ala His Glu Thr Ala Asn
            20                  25                  30

Ser Lys Ser Thr Ile Asp Asn Glu Val Ser Tyr Met Thr Arg Asn Trp
        35                  40                  45

Lys Asn Ala Phe Val Thr His Phe Val Gly Gly Gly Arg Val Val
    50                  55                  60
```

```
Gln Val Ala Asn Val Asn Tyr Val Ser Trp Gly Ala Gly Gln Tyr Ala
 65                  70                  75                  80

Asn Ser Tyr Ser Tyr Ala Gln Val Glu Leu Cys Lys Thr Ser Asn Ala
                 85                  90                  95

Thr Thr Phe Lys Lys Asp Tyr Glu Val Tyr Cys Gln Leu Leu Val Asp
            100                 105                 110

Leu Ala Lys Lys Ala Gly Ile Pro Ile Thr Leu Asp Ser Gly Ser Lys
        115                 120                 125

Thr Ser Asp Lys Gly Ile Lys Ser His Lys Trp Val Ala Asp Lys Leu
    130                 135                 140

Gly Gly Thr Thr His Gln Asp Pro Tyr Ala Tyr Leu Ser Ser Trp Gly
145                 150                 155                 160

Ile Ser Lys Ala Gln Phe Ala Ser Asp Leu Ala Lys Val Ser Gly Gly
                165                 170                 175

Gly Asn Thr Gly Thr Ala Pro Ala Lys Pro Ser Thr Pro Ala Pro Lys
            180                 185                 190

Pro Ser Thr Pro Ser Thr Asn Leu Asp Lys Leu Gly Leu Val Asp Tyr
        195                 200                 205

Met Asn Ala Lys Lys Met Asp Ser Ser Tyr Ser Asn Lys Asp Lys Leu
    210                 215                 220

Ala Lys Gln Tyr Gly Ile Ala Asn Tyr Ser Gly Thr Ala Ser Gln Asn
225                 230                 235                 240

Thr Thr Leu Leu Ser Lys Ile Lys Gly Gly Ala Pro Lys Pro Ser Thr
                245                 250                 255

Pro Ala Pro Lys Pro Ser Thr Ser Thr Ala Lys Lys Ile Tyr Phe Pro
            260                 265                 270

Pro Asn Lys Gly Asn Trp Ser Val Tyr Pro Thr Asn Lys Ala Pro Val
        275                 280                 285

Lys Ala Asn Ala Ile Gly Ala Ile Asn Pro Thr Lys Phe Gly Gly Leu
    290                 295                 300

Thr Tyr Thr Ile Gln Lys Asp Arg Gly Asn Gly Val Tyr Glu Ile Gln
305                 310                 315                 320

Thr Asp Gln Phe Gly Arg Val Gln Val Tyr Gly Ala Pro Ser Thr Gly
                325                 330                 335

Ala Val Ile Lys Lys
            340

<210> SEQ ID NO 8
<211> LENGTH: 341
<212> TYPE: PRT
<213> ORGANISM: artificial
<220> FEATURE:
<223> OTHER INFORMATION: Synthetic peptide

<400> SEQUENCE: 8

Met Val Lys Tyr Thr Val Glu Asn Lys Ile Ala Gly Leu Pro Lys
 1               5                  10                  15

Gly Lys Leu Lys Gly Ala Asn Phe Val Ile Ala His Glu Thr Ala Asn
                 20                  25                  30

Ser Lys Ser Thr Ile Asp Asn Glu Val Ser Tyr Met Thr Arg Asn Trp
             35                  40                  45

Lys Asn Ala Phe Val Thr His Phe Val Gly Gly Gly Arg Val Val
     50                  55                  60

Gln Val Ala Asn Val Asn Tyr Val Ser Trp Gly Ala Gly Gln Tyr Ala
 65                  70                  75                  80
```

```
Asn Ser Tyr Ser Tyr Ala Gln Val Glu Leu Cys Ala Thr Ser Asn Ala
                 85                  90                  95

Thr Thr Phe Lys Lys Asp Tyr Glu Val Tyr Cys Gln Leu Leu Val Asp
            100                 105                 110

Leu Ala Lys Lys Ala Gly Ile Pro Ile Thr Leu Asp Ser Gly Ser Lys
        115                 120                 125

Thr Ser Asp Lys Gly Ile Lys Ser His Lys Trp Val Ala Asp Lys Leu
    130                 135                 140

Gly Gly Thr Thr His Gln Asp Pro Tyr Ala Tyr Leu Ser Ser Trp Gly
145                 150                 155                 160

Ile Ser Lys Ala Gln Phe Ala Ser Asp Leu Ala Lys Val Ser Gly Gly
                165                 170                 175

Gly Asn Thr Gly Thr Ala Pro Ala Lys Pro Ser Thr Pro Ala Pro Lys
            180                 185                 190

Pro Ser Thr Pro Ser Thr Asn Leu Asp Lys Leu Gly Leu Val Asp Tyr
        195                 200                 205

Met Asn Ala Lys Lys Met Asp Ser Ser Tyr Ser Asn Ala Asp Lys Leu
    210                 215                 220

Ala Lys Gln Tyr Gly Ile Ala Asn Tyr Ser Gly Thr Ala Ser Gln Asn
225                 230                 235                 240

Thr Thr Leu Leu Ser Lys Ile Lys Gly Gly Ala Pro Lys Pro Ser Thr
                245                 250                 255

Pro Ala Pro Lys Pro Ser Thr Ser Thr Ala Lys Lys Ile Tyr Phe Pro
            260                 265                 270

Pro Asn Lys Gly Asn Trp Ser Val Tyr Pro Thr Asn Lys Ala Pro Val
        275                 280                 285

Lys Ala Asn Ala Ile Gly Ala Ile Asn Pro Thr Lys Phe Gly Gly Leu
    290                 295                 300

Thr Tyr Thr Ile Gln Lys Asp Arg Gly Asn Gly Val Tyr Glu Ile Gln
305                 310                 315                 320

Thr Asp Gln Phe Gly Arg Val Gln Val Tyr Gly Ala Pro Ser Thr Gly
                325                 330                 335

Ala Val Ile Lys Lys
            340

<210> SEQ ID NO 9
<211> LENGTH: 317
<212> TYPE: PRT
<213> ORGANISM: artificial
<220> FEATURE:
<223> OTHER INFORMATION: Synthetic peptide

<400> SEQUENCE: 9

Met Ala Tyr Lys Val Glu Arg Arg Ile Arg Pro Gly Leu Pro Gln Val
1               5                   10                  15

Gly Tyr Ala Pro Tyr Gly Gln Val His Ala His Ser Thr Gly Asn Pro
            20                  25                  30

Arg Ser Thr Ala Gln Asn Glu Ala Asp Tyr Phe Gln Thr Lys Asp Ile
        35                  40                  45

Thr Thr Gly Phe Tyr Thr His Leu Val Gly Asn Gly Arg Val Ile Gln
    50                  55                  60

Leu Ala Glu Val Asn Arg Gly Ala Trp Asp Val Gly Gly Gly Trp Asn
65                  70                  75                  80

Gln Trp Gly Tyr Ala Ser Val Glu Leu Ile Glu Ser His Ser Asn Arg
                85                  90                  95
```

-continued

```
Asp Glu Phe Met Arg Asp Tyr Lys Ile Tyr Cys Glu Leu Leu His Glu
            100                 105                 110
Leu Ala Lys Gln Ala Gly Leu Pro Thr Thr Val Asp Gln Gly Asn Thr
        115                 120                 125
Gly Ile Ile Thr His Asn Tyr Ala Thr His Asn Gln Pro Asn Asn Gly
    130                 135                 140
Ser Asp His Val Asp Pro Ile Pro Tyr Leu Ala Lys Trp Gly Ile Asn
145                 150                 155                 160
Leu Ala Gln Phe Arg Ser Asp Val Ala Asn Ala Lys Ser Asn Ser Lys
                165                 170                 175
Pro Val Thr Pro Ser Lys Pro Val Ser His Asp Lys Ala Ile Ala Lys
            180                 185                 190
Ser Pro Ala Lys Thr Val Asn Gly Tyr Thr Gly Lys Met Asp Lys Phe
        195                 200                 205
Asn Val Gln Gly Asn Lys Phe Arg Val Ala Gly Trp Met Leu Pro Thr
    210                 215                 220
Ala Gly Gly Gln Pro Tyr Asn Tyr Gly Tyr Val Phe Leu Leu Asp Ala
225                 230                 235                 240
Lys Thr Gly Lys Glu Ile Ala Arg Gln Leu Ala Gly Ala Val Ser Arg
                245                 250                 255
Pro Asp Val Thr Lys Ala Tyr Gly Val Lys Gly Gly Thr Asn Tyr Gly
            260                 265                 270
Leu Asp Val Thr Phe Asp Val Lys Leu Lys Gly Lys Lys Phe Tyr
        275                 280                 285
Ala Met Phe Arg Arg Thr Asn Asp Lys Ala Gly Asn Thr Ala Gly Gly
    290                 295                 300
His Lys Asp Ile Gly Phe Asn Glu Phe Tyr Phe Thr Leu
305                 310                 315

<210> SEQ ID NO 10
<211> LENGTH: 317
<212> TYPE: PRT
<213> ORGANISM: artificial
<220> FEATURE:
<223> OTHER INFORMATION: Synthetic peptide

<400> SEQUENCE: 10

Met Ala Tyr Lys Val Glu Arg Arg Ile Arg Pro Gly Leu Pro Gln Val
1               5                  10                  15
Gly Tyr Ala Pro Tyr Gly Gln Val His Ala His Ser Thr Gly Asn Pro
            20                  25                  30
Arg Ser Thr Ala Gln Asn Glu Ala Asp Tyr Phe Gln Thr Lys Asp Ile
        35                  40                  45
Thr Thr Gly Phe Tyr Thr His Leu Val Gly Asn Gly Arg Val Ile Gln
    50                  55                  60
Leu Ala Glu Val Asn Arg Gly Ala Trp Asp Val Gly Gly Gly Trp Asn
65                  70                  75                  80
Gln Trp Gly Tyr Ala Ser Val Glu Leu Ile Glu Ser His Ser Asn Arg
                85                  90                  95
Asp Glu Phe Met Arg Asp Tyr Lys Ile Tyr Cys Glu Leu Leu His Ala
            100                 105                 110
Leu Ala Lys Gln Ala Gly Leu Pro Thr Thr Val Asp Gln Gly Asn Thr
        115                 120                 125
Gly Ile Ile Thr His Asn Tyr Ala Thr His Asn Gln Pro Asn Asn Gly
    130                 135                 140
```

```
Ser Asp His Val Asp Pro Ile Pro Tyr Leu Ala Lys Trp Gly Ile Asn
145                 150                 155                 160

Leu Ala Gln Phe Arg Ser Asp Val Ala Asn Ala Lys Ser Asn Ser Lys
                165                 170                 175

Pro Val Thr Pro Ser Lys Pro Val Ser His Asp Lys Ala Ile Ala Lys
            180                 185                 190

Ser Pro Ala Lys Thr Val Asn Gly Tyr Thr Gly Lys Met Asp Lys Phe
            195                 200                 205

Asn Val Gln Gly Asn Lys Phe Arg Val Ala Gly Trp Met Leu Pro Thr
210                 215                 220

Ala Gly Gly Gln Pro Tyr Asn Tyr Gly Tyr Val Phe Leu Leu Asp Ala
225                 230                 235                 240

Lys Thr Gly Lys Glu Ile Ala Arg Gln Leu Ala Gly Ala Val Ser Arg
                245                 250                 255

Pro Asp Val Thr Lys Ala Tyr Gly Val Lys Gly Thr Asn Tyr Gly
            260                 265                 270

Leu Asp Val Thr Phe Asp Val Lys Leu Lys Gly Lys Lys Phe Tyr
                275                 280                 285

Ala Met Phe Arg Arg Thr Asn Asp Lys Ala Gly Asn Thr Ala Gly Gly
290                 295                 300

His Lys Asp Ile Gly Phe Asn Glu Phe Tyr Phe Thr Leu
305                 310                 315
```

<210> SEQ ID NO 11
<211> LENGTH: 496
<212> TYPE: PRT
<213> ORGANISM: artificial
<220> FEATURE:
<223> OTHER INFORMATION: Synthetic peptide

<400> SEQUENCE: 11

```
Met Ser Ile Ile Met Glu Val Ala Thr Met Gln Ala Lys Leu Thr Lys
1               5                   10                  15

Lys Glu Phe Ile Glu Trp Leu Lys Thr Ser Glu Gly Lys Gln Phe Asn
                20                  25                  30

Val Asp Leu Trp Tyr Gly Phe Gln Cys Phe Asp Tyr Ala Asn Ala Gly
            35                  40                  45

Trp Lys Val Leu Phe Gly Leu Leu Lys Gly Leu Gly Ala Lys Asp
50                  55                  60

Ile Pro Phe Ala Asn Asn Phe Asp Gly Leu Ala Thr Val Tyr Gln Asn
65                  70                  75                  80

Thr Pro Asp Phe Leu Ala Gln Pro Gly Asp Met Val Val Phe Gly Ser
                85                  90                  95

Asn Tyr Gly Ala Gly Tyr Gly His Val Ala Trp Val Ile Glu Ala Thr
                100                 105                 110

Leu Asp Tyr Ile Ile Val Tyr Glu Gln Asn Trp Leu Gly Gly Gly Trp
            115                 120                 125

Thr Asp Arg Ile Glu Gln Pro Gly Trp Gly Trp Glu Lys Val Thr Arg
130                 135                 140

Arg Gln His Ala Tyr Asp Phe Pro Met Trp Phe Ile Arg Pro Asn Phe
145                 150                 155                 160

Lys Ser Gln Thr Ala Pro Ala Ser Ile Gln Ser Pro Thr Gln Ala Ser
                165                 170                 175

Lys Lys Glu Thr Ala Lys Pro Gln Pro Lys Ala Val Glu Leu Lys Ile
                180                 185                 190
```

```
            Ile Lys Asp Val Val Lys Gly Tyr Asp Leu Pro Lys Arg Gly Gly Asn
                195                 200                 205

Pro Lys Gly Ile Val Ile His Asn Asp Ala Gly Ser Lys Gly Ala Thr
            210                 215                 220

Ala Glu Ala Tyr Arg Asn Gly Leu Val Asn Ala Pro Ser Ser Arg Leu
            225                 230                 235                 240

Glu Ala Gly Ile Ala His Ser Tyr Val Ser Gly Asn Thr Val Trp Gln
                            245                 250                 255

Ala Leu Asp Glu Ser Gln Val Gly Trp His Thr Ala Asn Gln Leu Gly
                            260                 265                 270

Asn Lys Tyr Tyr Tyr Gly Ile Glu Val Cys Ser Met Gly Ala Asp
                        275                 280                 285

Asn Ala Thr Phe Leu Lys Asn Glu Gln Ala Thr Phe Gln Glu Cys Ala
            290                 295                 300

Arg Leu Leu Lys Lys Trp Gly Leu Pro Ala Asn Arg Asn Thr Ile Arg
            305                 310                 315                 320

Leu His Asn Glu Phe Thr Ser Thr Ser Cys Pro His Arg Ser Ser Val
                            325                 330                 335

Leu His Thr Gly Phe Asp Pro Val Thr Arg Gly Leu Leu Pro Glu Asp
                        340                 345                 350

Lys Arg Leu Gln Leu Lys Asp Tyr Phe Ile Lys Gln Ile Arg Ala Tyr
                        355                 360                 365

Met Asp Gly Lys Ile Pro Val Ala Thr Val Ser Asn Glu Ser Ser Ala
            370                 375                 380

Ser Ser Asn Thr Val Lys Pro Val Ala Glu Leu Met Pro Pro Val Pro
            385                 390                 395                 400

Ala Gly Tyr Thr Leu Asp Lys Asn Asn Val Pro Tyr Lys Lys Glu Gln
                            405                 410                 415

Gly Asn Tyr Thr Val Ala Asn Val Lys Gly Asn Asn Val Arg Asp Gly
                        420                 425                 430

Tyr Ser Thr Asn Ser Arg Ile Thr Gly Val Leu Pro Asn Asn Thr Thr
                        435                 440                 445

Ile Thr Tyr Asp Gly Ala Tyr Cys Ile Asn Gly Tyr Arg Trp Ile Thr
            450                 455                 460

Tyr Ile Ala Asn Ser Gly Gln Arg Arg Tyr Ile Ala Thr Gly Glu Val
            465                 470                 475                 480

Asp Ile Ala Gly Asn Arg Ile Ser Ser Phe Gly Lys Phe Ser Ala Val
                            485                 490                 495

<210> SEQ ID NO 12
<211> LENGTH: 497
<212> TYPE: PRT
<213> ORGANISM: artificial
<220> FEATURE:
<223> OTHER INFORMATION: Synthetic peptide

<400> SEQUENCE: 12

Met Ala Ser Ile Ile Met Glu Val Ala Thr Met Gln Ala Lys Leu Thr
1               5                   10                  15

Lys Lys Glu Phe Ile Glu Trp Leu Lys Thr Ser Glu Gly Lys Gln Phe
                20                  25                  30

Asn Val Asp Leu Trp Tyr Gly Phe Gln Cys Phe Asp Tyr Ala Asn Ala
            35                  40                  45

Gly Trp Lys Val Leu Phe Gly His Thr Leu Lys Gly Leu Gly Ala Lys
        50                  55                  60
```

```
Asp Ile Pro Phe Ala Asn Asn Phe Asp Gly Leu Ala Thr Val Tyr Gln
 65                  70                  75                  80

Asn Thr Pro Asp Phe Leu Ala Gln Pro Gly Asp Met Val Val Phe Gly
                 85                  90                  95

Ser Asn Tyr Gly Ala Gly Tyr Gly His Val Ala Trp Val Ile Glu Ala
            100                 105                 110

Thr Leu Asp Tyr Ile Ile Val Tyr Glu Gln Asn Trp Leu Gly Gly Gly
        115                 120                 125

Trp Thr Asp Arg Ile Glu Gln Pro Gly Trp Gly Trp Glu Lys Val Thr
130                 135                 140

Arg Arg Gln His Ala Tyr Asp Phe Pro Met Trp Phe Ile Arg Pro Asn
145                 150                 155                 160

Phe Lys Ser Ala Thr Ala Pro Ala Ser Ile Asn Ser Pro Thr Asn Ala
                165                 170                 175

Ser Lys Lys Glu Thr Ala Lys Pro Gln Pro Lys Ala Val Glu Leu Lys
            180                 185                 190

Ile Ile Lys Asp Val Val Lys Gly His Asp Leu Pro Lys Arg Gly Gly
        195                 200                 205

Asn Pro Lys Gly Ile Val Ile His Asn Asp Ala Gly Ser Lys Gly Ala
210                 215                 220

Thr Ala Glu Ala Tyr Arg Asn Gly Leu Val Asn Ala Pro Ser Ser Arg
225                 230                 235                 240

Leu Glu Ala Gly Ile Ala His Ser Tyr Val Ser Gly Asn Thr Val Trp
                245                 250                 255

Gln Ala Leu Asp Glu Ser Gln Val Gly Trp His Thr Ala Asn Gln Leu
            260                 265                 270

Gly Asn Lys Tyr Tyr Tyr Gly Ile Glu Val Cys Gln Ser Met Gly Ala
        275                 280                 285

Asp Asn Ala Thr Phe Leu Lys Asn Glu Gln Ala Thr Phe Gln Glu Cys
290                 295                 300

Ala Arg Leu Leu Lys Lys Trp Gly Leu Pro Ala Asn Arg Asn Thr Ile
305                 310                 315                 320

Arg Leu His Asn Glu Phe Thr Ser Thr Ser Cys Pro His Arg Ser Ser
                325                 330                 335

Val Leu His Thr Gly Phe Asp Pro Val Thr Arg Gly Leu Leu Pro Glu
            340                 345                 350

Asp Lys Arg Leu Gln Leu Lys Asp Tyr Phe Ile Lys Gln Ile Arg Ala
        355                 360                 365

Tyr Met Asp Gly Lys Ile Pro Val Ala Thr Val Ser Asn Glu Ser Thr
370                 375                 380

Ala Ser Ser Asn Thr Val Lys Pro Val Ala Glu Leu Met Pro Pro Val
385                 390                 395                 400

Pro Ala Gly Tyr Thr Leu Asp Lys Asn Asn Val Pro Tyr Lys Lys Glu
                405                 410                 415

Gln Gly Asn Tyr Thr Val Ala Asn Val Lys Gly Asn Asn Val Arg Asp
            420                 425                 430

Gly Tyr Ser Thr Asn Ser Arg Ile Thr Gly Val Leu Pro Asn Asn Thr
        435                 440                 445

Thr Ile Thr Tyr Asp Gly Ala Tyr Cys Ile Asn Gly Tyr Arg Trp Ile
450                 455                 460

Thr Tyr Ile Ala Asn Ser Gly Gln Arg Arg Tyr Ile Ala Thr Gly Glu
465                 470                 475                 480
```

Val Asp Ile Ala Gly Asn Arg Ile Ser Ser Phe Gly Lys Phe Ser Ala
            485                 490                 495

Val

<210> SEQ ID NO 13
<211> LENGTH: 497
<212> TYPE: PRT
<213> ORGANISM: artificial
<220> FEATURE:
<223> OTHER INFORMATION: Synthetic peptide

<400> SEQUENCE: 13

Met Ala Ser Ile Ile Met Glu Val Ala Thr Met Gln Ala Lys Leu Thr
1               5                  10                  15

Lys Lys Glu Phe Ile Glu Trp Leu Lys Thr Ser Glu Gly Lys Gln Phe
                20                  25                  30

Asn Val Asp Leu Trp Tyr Gly Phe Gln Cys Phe Asp Tyr Ala Asn Ala
            35                  40                  45

Gly Trp Lys Val Leu Phe Gly His Thr Leu Lys Gly Leu Gly Ala Lys
    50                  55                  60

Asp Ile Pro Phe Ala Asn Asn Phe Asp Gly Leu Ala Thr Val Tyr Gln
65                  70                  75                  80

Asn Thr Pro Asp Phe Leu Ala Gln Pro Gly Asp Met Val Val Phe Gly
                85                  90                  95

Ser Asn Tyr Gly Ala Gly Tyr Gly His Val Ala Trp Val Ile Glu Ala
            100                 105                 110

Thr Leu Asp Tyr Ile Ile Val Tyr Glu Gln Asn Trp Leu Gly Gly Gly
        115                 120                 125

Trp Thr Asp Arg Ile Glu Gln Pro Gly Trp Gly Trp Glu Lys Val Thr
130                 135                 140

Arg Arg Gln His Ala Tyr Asp Phe Pro Met Trp Phe Ile Arg Pro Asn
145                 150                 155                 160

Phe Lys Ser Ala Thr Ala Pro Ala Ser Ile Ala Ser Pro Thr Ala Ala
                165                 170                 175

Ser Lys Lys Glu Thr Ala Lys Pro Gln Pro Lys Ala Val Glu Leu Lys
            180                 185                 190

Ile Ile Lys Asp Val Val Lys Gly His Asp Leu Pro Lys Arg Gly Gly
        195                 200                 205

Asn Pro Lys Gly Ile Val Ile His Asn Asp Ala Gly Ser Lys Gly Ala
210                 215                 220

Thr Ala Glu Ala Tyr Arg Asn Gly Leu Val Asn Ala Pro Ser Ser Arg
225                 230                 235                 240

Leu Glu Ala Gly Ile Ala His Ser Tyr Val Ser Gly Asn Thr Val Trp
                245                 250                 255

Gln Ala Leu Asp Glu Ser Gln Val Gly Trp His Thr Ala Asn Gln Leu
            260                 265                 270

Gly Asn Lys Tyr Tyr Tyr Gly Ile Glu Val Cys Gln Ser Met Gly Ala
        275                 280                 285

Asp Asn Ala Thr Phe Leu Lys Asn Glu Gln Ala Thr Phe Gln Glu Cys
290                 295                 300

Ala Arg Leu Leu Lys Lys Trp Gly Leu Pro Ala Asn Arg Asn Thr Ile
305                 310                 315                 320

Arg Leu His Asn Glu Phe Thr Ser Thr Ser Cys Pro His Arg Ser Ser
                325                 330                 335

Val Leu His Thr Gly Phe Asp Pro Val Thr Arg Gly Leu Leu Pro Glu
            340                 345                 350

```
Asp Lys Arg Leu Gln Leu Lys Asp Tyr Phe Ile Lys Gln Ile Arg Ala
        355                 360                 365

Tyr Met Asp Gly Lys Ile Pro Val Ala Thr Val Ser Asn Glu Ser Ala
    370                 375                 380

Ala Ser Ser Asn Thr Val Lys Pro Val Ala Glu Leu Met Pro Pro Val
385                 390                 395                 400

Pro Ala Gly Tyr Thr Leu Asp Lys Asn Asn Val Pro Tyr Lys Lys Glu
                405                 410                 415

Gln Gly Asn Tyr Thr Val Ala Asn Val Lys Gly Asn Asn Val Arg Asp
            420                 425                 430

Gly Tyr Ser Thr Asn Ser Arg Ile Thr Gly Val Leu Pro Asn Asn Thr
        435                 440                 445

Thr Ile Thr Tyr Asp Gly Ala Tyr Cys Ile Asn Gly Tyr Arg Trp Ile
    450                 455                 460

Thr Tyr Ile Ala Asn Ser Gly Gln Arg Arg Tyr Ile Ala Thr Gly Glu
465                 470                 475                 480

Val Asp Ile Ala Gly Asn Arg Ile Ser Ser Phe Gly Lys Phe Ser Ala
                485                 490                 495

Val

<210> SEQ ID NO 14
<211> LENGTH: 497
<212> TYPE: PRT
<213> ORGANISM: artificial
<220> FEATURE:
<223> OTHER INFORMATION: Synthetic peptide

<400> SEQUENCE: 14

Met Ala Ser Ile Ile Met Glu Val Ala Thr Met Gln Ala Lys Leu Thr
1               5                   10                  15

Lys Lys Glu Phe Ile Glu Trp Leu Lys Thr Ser Glu Gly Lys Gln Phe
                20                  25                  30

Asn Val Asp Leu Trp Tyr Gly Phe Gln Cys Phe Asp Tyr Ala Asn Ala
            35                  40                  45

Gly Trp Lys Val Leu Phe Gly Leu Leu Leu Lys Gly Leu Gly Ala Lys
        50                  55                  60

Asp Ile Pro Phe Ala Asn Asn Phe Asp Gly Leu Ala Thr Val Tyr Gln
65                  70                  75                  80

Asn Thr Pro Asp Phe Leu Ala Gln Pro Gly Asp Met Val Val Phe Gly
                85                  90                  95

Ser Asn Tyr Gly Ala Gly Tyr Gly His Val Ala Trp Val Ile Glu Ala
                100                 105                 110

Thr Leu Asp Tyr Ile Ile Val Tyr Glu Gln Asn Trp Leu Gly Gly Gly
            115                 120                 125

Trp Thr Asp Arg Ile Glu Gln Pro Gly Trp Gly Trp Glu Lys Val Thr
        130                 135                 140

Arg Arg Gln His Ala Tyr Asp Phe Pro Met Trp Phe Ile Arg Pro Asn
145                 150                 155                 160

Phe Lys Ser Glu Thr Ala Pro Ala Ser Ile Gln Ser Pro Thr Gln Ala
                165                 170                 175

Ser Lys Lys Glu Thr Ala Lys Pro Gln Pro Lys Ala Val Glu Leu Lys
            180                 185                 190

Ile Ile Lys Asp Val Val Lys Gly Tyr Asp Leu Pro Lys Arg Gly Gly
        195                 200                 205

Asn Pro Lys Gly Ile Val Ile His Asn Asp Ala Gly Ser Lys Gly Ala
    210                 215                 220
```

```
Thr Ala Glu Ala Tyr Arg Asn Gly Leu Val Asn Ala Pro Ser Ser Arg
225                 230                 235                 240

Leu Glu Ala Gly Ile Ala His Ser Tyr Val Ser Gly Asn Thr Val Trp
            245                 250                 255

Gln Ala Leu Asp Glu Ser Gln Val Gly Trp His Thr Ala Asn Gln Leu
        260                 265                 270

Gly Asn Lys Tyr Tyr Tyr Gly Ile Glu Val Cys Gln Ser Met Gly Ala
    275                 280                 285

Asp Asn Ala Thr Phe Leu Lys Asn Glu Gln Ala Thr Phe Gln Glu Cys
290                 295                 300

Ala Arg Leu Leu Lys Lys Trp Gly Leu Pro Ala Asn Arg Asn Thr Ile
305                 310                 315                 320

Arg Leu His Asn Glu Phe Thr Ser Thr Ser Cys Pro His Arg Ser Ser
            325                 330                 335

Val Leu His Thr Gly Phe Asp Pro Val Thr Arg Gly Leu Leu Pro Glu
        340                 345                 350

Asp Lys Arg Leu Gln Leu Lys Asp Tyr Phe Ile Lys Gln Ile Arg Ala
    355                 360                 365

Tyr Met Asp Gly Lys Ile Pro Val Ala Thr Val Ser Asn Glu Ser Ser
370                 375                 380

Ala Ser Ser Asn Thr Val Lys Pro Val Ala Glu Leu Met Pro Pro Val
385                 390                 395                 400

Pro Ala Gly Tyr Thr Leu Asp Lys Asn Asn Val Pro Tyr Lys Lys Glu
            405                 410                 415

Gln Gly Asn Tyr Thr Val Ala Asn Val Lys Gly Asn Asn Val Arg Asp
        420                 425                 430

Gly Tyr Ser Thr Asn Ser Arg Ile Thr Gly Val Leu Pro Asn Asn Thr
    435                 440                 445

Thr Ile Thr Tyr Asp Gly Ala Tyr Cys Ile Asn Gly Tyr Arg Trp Ile
450                 455                 460

Thr Tyr Ile Ala Asn Ser Gly Gln Arg Arg Tyr Ile Ala Thr Gly Glu
465                 470                 475                 480

Val Asp Ile Ala Gly Asn Arg Ile Ser Ser Phe Gly Lys Phe Ser Ala
            485                 490                 495

Val

<210> SEQ ID NO 15
<211> LENGTH: 497
<212> TYPE: PRT
<213> ORGANISM: artificial
<220> FEATURE:
<223> OTHER INFORMATION: Synthetic peptide

<400> SEQUENCE: 15

Met Ala Ser Ile Ile Met Glu Val Ala Thr Met Gln Ala Lys Leu Thr
1               5                   10                  15

Lys Lys Glu Phe Ile Glu Trp Leu Lys Thr Ser Glu Gly Lys Gln Phe
            20                  25                  30

Asn Val Asp Leu Trp Tyr Gly Phe Gln Cys Phe Asp Tyr Ala Asn Ala
        35                  40                  45

Gly Trp Lys Val Leu Phe Gly Leu Leu Leu Lys Gly Leu Gly Ala Lys
    50                  55                  60

Asp Ile Pro Phe Ala Asn Asn Phe Asp Gly Leu Ala Thr Val Tyr Gln
65                  70                  75                  80
```

-continued

```
Asn Thr Pro Asp Phe Leu Ala Gln Pro Gly Asp Met Val Val Phe Gly
                85                  90                  95
Ser Asn Tyr Gly Ala Gly Tyr Gly His Val Ala Trp Val Ile Glu Ala
            100                 105                 110
Thr Leu Asp Tyr Ile Ile Val Tyr Glu Gln Asn Trp Leu Gly Gly Gly
            115                 120                 125
Trp Thr Asp Arg Ile Glu Gln Pro Gly Trp Gly Trp Glu Lys Val Thr
            130                 135                 140
Arg Arg Gln His Ala Tyr Asp Phe Pro Met Trp Phe Ile Arg Pro Asn
145                 150                 155                 160
Phe Lys Ser Ala Thr Ala Pro Ala Ser Ile Gln Ser Pro Thr Gln Ala
                165                 170                 175
Ser Lys Lys Glu Thr Ala Lys Pro Gln Pro Lys Ala Val Glu Leu Lys
            180                 185                 190
Ile Ile Lys Asp Val Val Lys Gly Tyr Asp Leu Pro Lys Arg Gly Gly
            195                 200                 205
Asn Pro Lys Gly Ile Val Ile His Asn Asp Ala Gly Ser Lys Gly Ala
210                 215                 220
Thr Ala Glu Ala Tyr Arg Asn Gly Leu Val Asn Ala Pro Ser Ser Arg
225                 230                 235                 240
Leu Glu Ala Gly Ile Ala His Ser Tyr Val Ser Gly Asn Thr Val Trp
                245                 250                 255
Gln Ala Leu Asp Glu Ser Gln Val Gly Trp His Thr Ala Asn Gln Leu
            260                 265                 270
Gly Asn Lys Tyr Tyr Gly Ile Glu Val Cys Gln Ser Met Gly Ala
            275                 280                 285
Asp Asn Ala Thr Phe Leu Lys Asn Glu Gln Ala Thr Phe Gln Glu Cys
290                 295                 300
Ala Arg Leu Leu Lys Lys Trp Gly Leu Pro Ala Asn Arg Asn Thr Ile
305                 310                 315                 320
Arg Leu His Asn Glu Phe Thr Ser Thr Ser Cys Pro His Arg Ser Ser
                325                 330                 335
Val Leu His Thr Gly Phe Asp Pro Val Thr Arg Gly Leu Leu Pro Glu
            340                 345                 350
Asp Lys Arg Leu Gln Leu Lys Asp Tyr Phe Ile Lys Gln Ile Arg Ala
            355                 360                 365
Tyr Met Asp Gly Lys Ile Pro Val Ala Thr Val Ser Asn Glu Ser Ser
370                 375                 380
Ala Ser Ser Asn Thr Val Lys Pro Val Ala Glu Leu Met Pro Pro Val
385                 390                 395                 400
Pro Ala Gly Tyr Thr Leu Asp Lys Asn Asn Val Pro Tyr Lys Lys Glu
                405                 410                 415
Gln Gly Asn Tyr Thr Val Ala Asn Val Lys Gly Asn Asn Val Arg Asp
            420                 425                 430
Gly Tyr Ser Thr Asn Ser Arg Ile Thr Gly Val Leu Pro Asn Asn Thr
            435                 440                 445
Thr Ile Thr Tyr Asp Gly Ala Tyr Cys Ile Asn Gly Tyr Arg Trp Ile
            450                 455                 460
Thr Tyr Ile Ala Asn Ser Gly Gln Arg Arg Tyr Ile Ala Thr Gly Glu
465                 470                 475                 480
Val Asp Ile Ala Gly Asn Arg Ile Ser Ser Phe Gly Lys Phe Ser Ala
                485                 490                 495
Val
```

```
<210> SEQ ID NO 16
<211> LENGTH: 497
<212> TYPE: PRT
<213> ORGANISM: artificial
<220> FEATURE:
<223> OTHER INFORMATION: Synthetic peptide

<400> SEQUENCE: 16

Met Ala Ser Ile Ile Met Glu Val Ala Thr Met Gln Ala Lys Leu Thr
1               5                   10                  15

Lys Lys Glu Phe Ile Glu Trp Leu Lys Thr Ser Glu Gly Lys Gln Phe
            20                  25                  30

Asn Val Asp Leu Trp Tyr Gly Phe Gln Cys Phe Asp Tyr Ala Asn Ala
        35                  40                  45

Gly Trp Lys Val Leu Phe Gly Leu Leu Leu Lys Gly Leu Gly Ala Lys
    50                  55                  60

Asp Ile Pro Phe Ala Asn Asn Phe Asp Gly Leu Ala Thr Val Tyr Gln
65                  70                  75                  80

Asn Thr Pro Asp Phe Leu Ala Gln Pro Gly Asp Met Val Val Phe Gly
                85                  90                  95

Ser Asn Tyr Gly Ala Gly Tyr Gly His Val Ala Trp Val Ile Glu Ala
            100                 105                 110

Thr Leu Asp Tyr Ile Ile Val Tyr Glu Gln Asn Trp Leu Gly Gly Gly
        115                 120                 125

Trp Thr Asp Arg Ile Glu Gln Pro Gly Trp Gly Trp Glu Lys Val Thr
130                 135                 140

Arg Arg Gln His Ala Tyr Asp Phe Pro Met Trp Phe Ile Arg Pro Asn
145                 150                 155                 160

Phe Lys Ser Gln Thr Ala Pro Ala Ser Ile Gln Ser Pro Thr Gln Ala
                165                 170                 175

Ser Lys Lys Ala Thr Ala Lys Pro Gln Pro Lys Ala Val Gln Leu Lys
            180                 185                 190

Ile Ile Lys Asp Val Val Lys Gly Tyr Asp Leu Pro Lys Arg Gly Gly
        195                 200                 205

Asn Pro Lys Gly Ile Val Ile His Asn Asp Ala Gly Ser Lys Gly Ala
    210                 215                 220

Thr Ala Glu Ala Tyr Arg Asn Gly Leu Val Asn Ala Pro Ser Ser Arg
225                 230                 235                 240

Leu Glu Ala Gly Ile Ala His Ser Tyr Val Ser Gly Asn Thr Val Trp
                245                 250                 255

Gln Ala Leu Asp Glu Ser Gln Val Gly Trp His Thr Ala Asn Gln Leu
            260                 265                 270

Gly Asn Lys Tyr Tyr Tyr Gly Ile Glu Val Cys Gln Ser Met Gly Ala
        275                 280                 285

Asp Asn Ala Thr Phe Leu Lys Asn Glu Gln Ala Thr Phe Gln Glu Cys
    290                 295                 300

Ala Arg Leu Leu Lys Lys Trp Gly Leu Pro Ala Asn Arg Asn Thr Ile
305                 310                 315                 320

Arg Leu His Asn Glu Phe Thr Ser Thr Ser Cys Pro His Arg Ser Ser
                325                 330                 335

Val Leu His Thr Gly Phe Asp Pro Val Thr Arg Gly Leu Leu Pro Glu
            340                 345                 350

Asp Lys Arg Leu Gln Leu Lys Asp Tyr Phe Ile Lys Gln Ile Arg Ala
        355                 360                 365

Tyr Met Asp Gly Lys Ile Pro Val Ala Thr Val Ser Asn Glu Ser Ser
    370                 375                 380
```

```
Ala Ser Ser Asn Thr Val Lys Pro Val Ala Glu Leu Met Pro Pro Val
385                 390                 395                 400

Pro Ala Gly Tyr Thr Leu Asp Lys Asn Asn Val Pro Tyr Lys Lys Glu
            405                 410                 415

Gln Gly Asn Tyr Thr Val Ala Asn Val Lys Gly Asn Asn Val Arg Asp
                420                 425                 430

Gly Tyr Ser Thr Asn Ser Arg Ile Thr Gly Val Leu Pro Asn Asn Thr
            435                 440                 445

Thr Ile Thr Tyr Asp Gly Ala Tyr Cys Ile Asn Gly Tyr Arg Trp Ile
450                 455                 460

Thr Tyr Ile Ala Asn Ser Gly Gln Arg Arg Tyr Ile Ala Thr Gly Glu
465                 470                 475                 480

Val Asp Ile Ala Gly Asn Arg Ile Ser Ser Phe Gly Lys Phe Ser Ala
            485                 490                 495

Val

<210> SEQ ID NO 17
<211> LENGTH: 497
<212> TYPE: PRT
<213> ORGANISM: artificial
<220> FEATURE:
<223> OTHER INFORMATION: Synthetic peptide

<400> SEQUENCE: 17

Met Ala Ser Ile Ile Met Glu Val Ala Thr Met Gln Ala Lys Leu Thr
1               5                   10                  15

Lys Lys Glu Phe Ile Glu Trp Leu Lys Thr Ser Glu Gly Lys Gln Phe
            20                  25                  30

Asn Val Asp Leu Trp Tyr Gly Phe Gln Cys Phe Asp Tyr Ala Asn Ala
        35                  40                  45

Gly Trp Lys Val Leu Phe Gly Leu Leu Leu Lys Gly Leu Gly Ala Lys
    50                  55                  60

Asp Ile Pro Phe Ala Asn Asn Phe Asp Gly Leu Ala Thr Val Tyr Gln
65                  70                  75                  80

Asn Thr Pro Asp Phe Leu Ala Gln Pro Gly Asp Met Val Val Phe Gly
                85                  90                  95

Ser Asn Tyr Gly Ala Gly Tyr Gly His Val Ala Trp Val Ile Glu Ala
            100                 105                 110

Thr Leu Asp Tyr Ile Ile Val Tyr Glu Gln Asn Trp Leu Gly Gly Gly
        115                 120                 125

Trp Thr Asp Arg Ile Glu Gln Pro Gly Trp Gly Trp Glu Lys Val Thr
    130                 135                 140

Arg Arg Gln His Ala Tyr Asp Phe Pro Met Trp Phe Ile Arg Pro Asn
145                 150                 155                 160

Phe Lys Ser Gln Thr Ala Pro Ala Ser Ile Gln Ser Pro Thr Gln Ala
                165                 170                 175

Ser Lys Lys Glu Thr Ala Lys Pro Gln Pro Lys Ala Val Glu Leu Lys
            180                 185                 190

Ile Ile Lys Asp Val Val Lys Gly Tyr Asp Leu Pro Arg Gly Gly
        195                 200                 205

Asn Pro Lys Gly Ile Val Ile His Asn Asp Ala Gly Ser Lys Gly Ala
    210                 215                 220

Thr Ala Glu Ala Tyr Arg Asn Gly Leu Val Asn Ala Pro Ser Ser Arg
225                 230                 235                 240

Leu Glu Ala Gly Ile Ala His Ser Tyr Val Ser Gly Asn Thr Val Trp
                245                 250                 255
```

```
Gln Ala Leu Asp Glu Ser Gln Val Gly Trp His Thr Ala Asn Gln Leu
            260                 265                 270

Gly Asn Lys Tyr Tyr Tyr Gly Ile Glu Val Cys Gln Ser Met Gly Ala
        275                 280                 285

Asp Asn Ala Thr Phe Leu Lys Asn Glu Gln Ala Thr Phe Gln Glu Cys
    290                 295                 300

Ala Arg Leu Leu Lys Lys Trp Gly Leu Pro Ala Asn Arg Asn Thr Ile
305                 310                 315                 320

Arg Leu His Asn Glu Phe Thr Ser Thr Ser Cys Pro His Arg Ser Ser
                325                 330                 335

Val Leu His Thr Gly Phe Asp Pro Val Thr Arg Gly Leu Leu Pro Glu
            340                 345                 350

Asp Lys Arg Leu Gln Leu Lys Asp Tyr Phe Ile Lys Gln Ile Arg Ala
        355                 360                 365

Tyr Met Asp Gly Lys Ile Pro Val Ala Thr Val Ser Asn Glu Ser Ser
    370                 375                 380

Ala Ser Ser Asn Thr Val Lys Pro Val Ala Glu Leu Met Pro Pro Val
385                 390                 395                 400

Pro Ala Gly Tyr Thr Leu Asp Lys Asn Asn Val Pro Tyr Lys Lys Glu
                405                 410                 415

Gln Gly Asn Tyr Thr Val Ala Asn Val Lys Gly Asn Asn Val Arg Asp
            420                 425                 430

Gly Tyr Ser Thr Asn Ser Arg Ile Thr Gly Val Leu Pro Asn Asn Thr
        435                 440                 445

Thr Ile Thr Tyr Asp Gly Ala Tyr Cys Ile Asn Gly Tyr Arg Trp Ile
450                 455                 460

Thr Tyr Ile Ala Asn Ser Gly Gln Arg Arg Tyr Ile Ala Thr Gly Glu
465                 470                 475                 480

Val Asp Ile Ala Gly Asn Arg Ile Ser Ser Phe Gly Lys Phe Ser Ala
                485                 490                 495

Val

<210> SEQ ID NO 18
<211> LENGTH: 496
<212> TYPE: PRT
<213> ORGANISM: artificial
<220> FEATURE:
<223> OTHER INFORMATION: Synthetic peptide

<400> SEQUENCE: 18

Met Ser Ile Ile Met Glu Val Ala Thr Met Gln Ala Lys Leu Thr Lys
1               5                   10                  15

Lys Glu Phe Ile Glu Trp Leu Lys Thr Ser Glu Gly Lys Gln Phe Asn
            20                  25                  30

Val Asp Leu Trp Tyr Gly Phe Gln Cys Phe Asp Tyr Ala Asn Ala Gly
        35                  40                  45

Trp Lys Val Leu Phe Gly Leu Leu Lys Gly Leu Gly Ala Lys Asp
    50                  55                  60

Ile Pro Phe Ala Asn Asn Phe Asp Gly Leu Ala Thr Val Tyr Gln Asn
65                  70                  75                  80

Thr Pro Asp Phe Leu Ala Gln Pro Gly Asp Met Val Val Phe Gly Ser
                85                  90                  95

Asn Tyr Gly Ala Gly Tyr Gly His Val Ala Trp Val Ile Glu Ala Thr
            100                 105                 110

Leu Asp Tyr Ile Ile Val Tyr Glu Gln Asn Trp Leu Gly Gly Gly Trp
        115                 120                 125
```

Thr Asp Arg Ile Glu Gln Pro Gly Trp Gly Trp Glu Lys Val Thr Arg
130              135                 140

Arg Gln His Ala Tyr Asp Phe Pro Met Trp Phe Ile Arg Pro Asn Phe
145                 150                 155                 160

Lys Ser Glu Thr Ala Pro Arg Ser Ile Gln Ser Pro Thr Gln Ala Ser
                165                 170                 175

Lys Lys Glu Thr Ala Lys Pro Gln Pro Lys Ala Val Glu Leu Lys Ile
            180                 185                 190

Ile Lys Asp Val Val Lys Gly Tyr Asp Leu Pro Lys Arg Gly Gly Asn
        195                 200                 205

Pro Lys Gly Ile Val Ile His Asn Asp Ala Gly Ser Lys Gly Ala Thr
210                 215                 220

Ala Glu Ala Tyr Arg Asn Gly Leu Val Asn Ala Pro Ser Ser Arg Leu
225                 230                 235                 240

Glu Ala Gly Ile Ala His Ser Tyr Val Ser Gly Asn Thr Val Trp Gln
                245                 250                 255

Ala Leu Asp Glu Ser Gln Val Gly Trp His Thr Ala Asn Gln Leu Gly
            260                 265                 270

Asn Lys Tyr Tyr Tyr Gly Ile Glu Val Cys Gln Ser Met Gly Ala Asp
        275                 280                 285

Asn Ala Thr Phe Leu Lys Asn Glu Gln Ala Thr Phe Gln Glu Cys Ala
290                 295                 300

Arg Leu Leu Lys Lys Trp Gly Leu Pro Ala Asn Arg Asn Thr Ile Arg
305                 310                 315                 320

Leu His Asn Glu Phe Thr Ser Thr Ser Cys Pro His Arg Ser Ser Val
                325                 330                 335

Leu His Thr Gly Phe Asp Pro Val Thr Arg Gly Leu Leu Pro Glu Asp
            340                 345                 350

Lys Arg Leu Gln Leu Lys Asp Tyr Phe Ile Lys Gln Ile Arg Ala Tyr
        355                 360                 365

Met Asp Gly Lys Ile Pro Val Ala Thr Val Ser Asn Glu Ser Ser Ala
370                 375                 380

Ser Ser Asn Thr Val Lys Pro Val Ala Glu Leu Met Pro Pro Val Pro
385                 390                 395                 400

Ala Gly Tyr Thr Leu Asp Lys Asn Asn Val Pro Tyr Lys Lys Glu Gln
                405                 410                 415

Gly Asn Tyr Thr Val Ala Asn Val Lys Gly Asn Asn Val Arg Asp Gly
            420                 425                 430

Tyr Ser Thr Asn Ser Arg Ile Thr Gly Val Leu Pro Asn Asn Thr Thr
        435                 440                 445

Ile Thr Tyr Asp Gly Ala Tyr Cys Ile Asn Gly Tyr Arg Trp Ile Thr
450                 455                 460

Tyr Ile Ala Asn Ser Gly Gln Arg Arg Tyr Ile Ala Thr Gly Glu Val
465                 470                 475                 480

Asp Ile Ala Gly Asn Arg Ile Ser Ser Phe Gly Lys Phe Ser Ala Val
                485                 490                 495

<210> SEQ ID NO 19
<211> LENGTH: 497
<212> TYPE: PRT
<213> ORGANISM: artificial
<220> FEATURE:
<223> OTHER INFORMATION: Synthetic peptide

<400> SEQUENCE: 19

```
Met Ala Ser Ile Ile Met Glu Val Ala Thr Met Gln Ala Lys Leu Thr
1               5                   10                  15

Lys Lys Glu Phe Ile Glu Trp Leu Lys Thr Ser Glu Gly Lys Gln Phe
            20                  25                  30

Asn Val Asp Leu Trp Tyr Gly Phe Gln Cys Phe Asp Tyr Ala Asn Ala
        35                  40                  45

Gly Trp Lys Val Leu Phe Gly Leu Leu Leu Lys Gly Leu Gly Ala Lys
    50                  55                  60

Asp Ile Pro Phe Ala Asn Asn Phe Asp Gly Leu Ala Thr Val Tyr Gln
65                  70                  75                  80

Asn Thr Pro Asp Phe Leu Ala Gln Pro Gly Asp Met Val Val Phe Gly
                85                  90                  95

Ser Asn Tyr Gly Ala Gly Tyr Gly His Val Ala Trp Val Ile Glu Ala
            100                 105                 110

Thr Leu Asp Tyr Ile Ile Val Tyr Glu Gln Asn Trp Leu Gly Gly Gly
        115                 120                 125

Trp Thr Asp Arg Ile Glu Gln Pro Gly Trp Gly Trp Glu Lys Val Thr
    130                 135                 140

Arg Arg Gln His Ala Tyr Asp Phe Pro Met Trp Phe Ile Arg Pro Asn
145                 150                 155                 160

Phe Lys Ser Glu Thr Ala Pro Arg Ser Ile Gln Ser Pro Thr Gln Ala
                165                 170                 175

Ser Lys Lys Glu Thr Ala Lys Pro Gln Pro Lys Ala Val Glu Leu Lys
            180                 185                 190

Ile Ile Lys Asp Val Val Lys Gly Tyr Asp Leu Pro Lys Arg Gly Gly
        195                 200                 205

Asn Pro Lys Gly Ile Val Ile His Asn Asp Ala Gly Ser Lys Gly Ala
    210                 215                 220

Thr Ala Glu Ala Tyr Arg Asn Gly Leu Val Asn Ala Pro Ser Ser Arg
225                 230                 235                 240

Leu Glu Ala Gly Ile Ala His Ser Tyr Val Ser Gly Asn Thr Val Trp
                245                 250                 255

Gln Ala Leu Asp Glu Ser Gln Val Gly Trp His Thr Ala Asn Gln Leu
            260                 265                 270

Gly Asn Lys Tyr Tyr Gly Ile Glu Val Cys Gln Ser Met Gly Ala
        275                 280                 285

Asp Asn Ala Thr Phe Leu Lys Asn Glu Gln Ala Thr Phe Gln Glu Cys
    290                 295                 300

Ala Arg Leu Leu Lys Lys Trp Gly Leu Pro Ala Asn Arg Asn Thr Ile
305                 310                 315                 320

Arg Leu His Asn Glu Phe Thr Ser Thr Ser Cys Pro His Arg Ser Ser
                325                 330                 335

Val Leu His Thr Gly Phe Asp Pro Val Thr Arg Gly Leu Leu Pro Glu
            340                 345                 350

Asp Lys Arg Leu Gln Leu Lys Asp Tyr Phe Ile Lys Gln Ile Arg Ala
        355                 360                 365

Tyr Met Asp Gly Lys Ile Pro Val Ala Thr Val Ser Asn Glu Ser Ser
    370                 375                 380

Ala Ser Ser Asn Thr Val Lys Pro Val Ala Glu Leu Met Pro Pro Val
385                 390                 395                 400

Pro Ala Gly Tyr Thr Leu Asp Lys Asn Asn Val Pro Tyr Lys Lys Glu
                405                 410                 415
```

Gln Gly Asn Tyr Thr Val Ala Asn Val Lys Gly Asn Asn Val Arg Asp
                420                 425                 430

Gly Tyr Ser Thr Asn Ser Arg Ile Thr Gly Val Leu Pro Asn Asn Thr
            435                 440                 445

Thr Ile Thr Tyr Asp Gly Ala Tyr Cys Ile Asn Gly Tyr Arg Trp Ile
450                 455                 460

Thr Tyr Ile Ala Asn Ser Gly Gln Arg Arg Tyr Ile Ala Thr Gly Glu
465                 470                 475                 480

Val Asp Ile Ala Gly Asn Arg Ile Ser Ser Phe Gly Lys Phe Ser Ala
                485                 490                 495

Val

<210> SEQ ID NO 20
<211> LENGTH: 393
<212> TYPE: PRT
<213> ORGANISM: artificial
<220> FEATURE:
<223> OTHER INFORMATION: Synthetic peptide

<400> SEQUENCE: 20

Met Ser Ile Ile Met Glu Val Ala Thr Met Gln Ala Lys Leu Thr Lys
1               5                   10                  15

Lys Glu Phe Ile Glu Trp Leu Lys Thr Ser Glu Gly Lys Gln Phe Asn
                20                  25                  30

Val Asp Leu Trp Tyr Gly Phe Gln Cys Phe Asp Tyr Ala Asn Ala Gly
            35                  40                  45

Trp Lys Val Leu Phe Gly Leu Leu Leu Lys Gly Leu Ala Lys Asp
50                  55                  60

Ile Pro Phe Ala Asn Asn Phe Asp Gly Leu Ala Thr Val Tyr Gln Asn
65                  70                  75                  80

Thr Pro Asp Phe Leu Ala Gln Pro Gly Asp Met Val Val Phe Gly Ser
                85                  90                  95

Asn Tyr Gly Ala Gly Tyr Gly His Val Ala Trp Val Ile Glu Ala Thr
            100                 105                 110

Leu Asp Tyr Ile Ile Val Tyr Glu Gln Asn Trp Leu Gly Gly Gly Trp
            115                 120                 125

Thr Asp Arg Ile Glu Gln Pro Gly Trp Gly Trp Glu Lys Val Thr Arg
130                 135                 140

Arg Gln His Ala Tyr Asp Phe Pro Met Trp Phe Ile Arg Pro Asn Phe
145                 150                 155                 160

Lys Ser Glu Thr Ala Pro Arg Ser Ile Gln Ser Pro Thr Gln Ala Ser
                165                 170                 175

Lys Lys Glu Thr Ala Lys Pro Gln Pro Lys Ala Val Glu Leu Lys Ile
            180                 185                 190

Ile Lys Asp Val Val Lys Gly Tyr Asp Leu Pro Lys Arg Gly Gly Asn
            195                 200                 205

Pro Lys Gly Ile Val Ile His Asn Asp Ala Gly Ser Lys Gly Ala Thr
210                 215                 220

Ala Glu Ala Tyr Arg Asn Gly Leu Val Asn Ala Pro Ser Ser Arg Leu
225                 230                 235                 240

Glu Ala Gly Ile Ala His Ser Tyr Val Ser Gly Asn Thr Val Trp Gln
                245                 250                 255

Ala Leu Asp Glu Ser Gln Val Gly Trp His Thr Ala Asn Gln Leu Gly
            260                 265                 270

Asn Lys Tyr Tyr Tyr Gly Ile Glu Val Cys Gln Ser Met Gly Ala Asp
            275                 280                 285

```
Asn Ala Thr Phe Leu Lys Asn Glu Gln Ala Thr Phe Gln Glu Cys Ala
            290                 295                 300

Arg Leu Leu Lys Lys Trp Gly Leu Pro Ala Asn Arg Asn Thr Ile Arg
305                 310                 315                 320

Leu His Asn Glu Phe Thr Ser Thr Ser Cys Pro His Arg Ser Ser Val
                325                 330                 335

Leu His Thr Gly Phe Asp Pro Val Thr Arg Gly Leu Leu Pro Glu Asp
            340                 345                 350

Lys Arg Leu Gln Leu Lys Asp Tyr Phe Ile Lys Gln Ile Arg Ala Tyr
                355                 360                 365

Met Asp Gly Lys Ile Pro Val Ala Thr Val Ser Asn Glu Ser Ser Ala
    370                 375                 380

Ser Ser Asn Thr Val Lys Pro Val Ala
385                 390

<210> SEQ ID NO 21
<211> LENGTH: 341
<212> TYPE: PRT
<213> ORGANISM: Artificial
<220> FEATURE:
<223> OTHER INFORMATION: Synthetic peptide

<400> SEQUENCE: 21

Met Val Lys Tyr Thr Val Glu Asn Lys Ile Ile Ala Gly Leu Pro Lys
1               5                   10                  15

Gly Lys Leu Lys Gly Ala Asn Phe Val Ile Ala His Glu Thr Ala Asn
                20                  25                  30

Ser Lys Ser Thr Ile Asp Asn Glu Val Ser Tyr Met Thr Arg Asn Trp
            35                  40                  45

Lys Asn Ala Phe Val Thr His Phe Val Gly Gly Gly Arg Val Val
    50                  55                  60

Gln Val Ala Asn Val Asn Tyr Val Ser Trp Gly Ala Gly Gln Tyr Ala
65                  70                  75                  80

Asn Ser Tyr Ser Tyr Ala Gln Val Glu Leu Cys Arg Thr Ser Asn Ala
                85                  90                  95

Thr Thr Phe Lys Lys Asp Tyr Glu Val Tyr Cys Gln Leu Leu Val Asp
                100                 105                 110

Leu Ala Lys Lys Ala Gly Ile Pro Ile Thr Leu Asp Ser Gly Ser Lys
            115                 120                 125

Thr Ser Asp Lys Gly Ile Lys Ser His Lys Trp Val Ala Asp Lys Leu
    130                 135                 140

Gly Gly Thr Thr His Gln Asp Pro Tyr Ala Tyr Leu Ser Ser Trp Gly
145                 150                 155                 160

Ile Ser Lys Ala Gln Phe Ala Ser Asp Leu Ala Lys Val Ser Gly Gly
                165                 170                 175

Gly Asn Thr Gly Thr Ala Pro Ala Lys Pro Ser Thr Pro Ala Pro Lys
            180                 185                 190

Pro Ser Thr Pro Ser Thr Asn Leu Asp Lys Leu Gly Leu Val Asp Tyr
    195                 200                 205

Met Asn Ala Lys Lys Met Asp Ser Ser Tyr Ser Asn Arg Asp Lys Leu
    210                 215                 220

Ala Lys Gln Tyr Gly Ile Ala Asn Tyr Ser Gly Thr Ala Ser Gln Asn
225                 230                 235                 240

Thr Thr Leu Leu Ser Lys Ile Lys Gly Gly Ala Pro Lys Pro Ser Thr
                245                 250                 255
```

```
Pro Ala Pro Lys Pro Ser Thr Ser Thr Ala Lys Lys Ile Tyr Phe Pro
                260                 265                 270

Pro Asn Lys Gly Asn Trp Ser Val Tyr Pro Thr Asn Lys Ala Pro Val
            275                 280                 285

Lys Ala Asn Ala Ile Gly Ala Ile Asn Pro Thr Lys Phe Gly Gly Leu
        290                 295                 300

Thr Tyr Thr Ile Gln Lys Asp Arg Gly Asn Gly Val Tyr Glu Ile Gln
305                 310                 315                 320

Thr Asp Gln Phe Gly Arg Val Gln Val Tyr Gly Ala Pro Ser Thr Gly
                325                 330                 335

Ala Val Ile Lys Lys
            340

<210> SEQ ID NO 22
<211> LENGTH: 497
<212> TYPE: PRT
<213> ORGANISM: artificial
<220> FEATURE:
<223> OTHER INFORMATION: Synthetic peptide

<400> SEQUENCE: 22

Met Ala Ser Ile Ile Met Glu Val Ala Thr Met Gln Ala Lys Leu Thr
1               5                   10                  15

Lys Lys Glu Phe Ile Glu Trp Leu Lys Thr Ser Glu Gly Lys Gln Phe
            20                  25                  30

Asn Val Asp Leu Trp Tyr Gly Phe Gln Cys Phe Asp Tyr Ala Asn Ala
        35                  40                  45

Gly Trp Lys Val Leu Phe Gly His Thr Leu Lys Gly Leu Gly Ala Lys
    50                  55                  60

Asp Ile Pro Phe Ala Asn Asn Phe Asp Gly Leu Ala Thr Val Tyr Gln
65                  70                  75                  80

Asn Thr Pro Asp Phe Leu Ala Gln Pro Gly Asp Met Val Val Phe Gly
                85                  90                  95

Ser Asn Tyr Gly Ala Gly Tyr Gly His Val Ala Trp Val Ile Glu Ala
            100                 105                 110

Thr Leu Asp Tyr Ile Ile Val Tyr Glu Gln Asn Trp Leu Gly Gly Gly
        115                 120                 125

Trp Thr Asp Arg Ile Glu Gln Pro Gly Trp Gly Trp Glu Lys Val Thr
130                 135                 140

Arg Arg Gln His Ala Tyr Asp Phe Pro Met Trp Phe Ile Arg Pro Asn
145                 150                 155                 160

Phe Lys Ser Ala Thr Ala Pro Ala Ser Ile Gln Ser Pro Thr Gln Ala
                165                 170                 175

Ser Lys Lys Glu Thr Ala Lys Pro Gln Pro Lys Ala Val Glu Leu Lys
            180                 185                 190

Ile Ile Lys Asp Val Val Lys Gly His Asp Leu Pro Lys Arg Gly Gly
        195                 200                 205

Asn Pro Lys Gly Ile Val Ile His Asn Asp Ala Gly Ser Lys Gly Ala
210                 215                 220

Thr Ala Glu Ala Tyr Arg Asn Gly Leu Val Asn Ala Pro Ser Ser Arg
225                 230                 235                 240

Leu Glu Ala Gly Ile Ala His Ser Tyr Val Ser Gly Asn Thr Val Trp
                245                 250                 255

Gln Ala Leu Asp Glu Ser Gln Val Gly Trp His Thr Ala Asn Gln Leu
            260                 265                 270
```

```
Gly Asn Lys Tyr Tyr Tyr Gly Ile Glu Val Cys Gln Ser Met Gly Ala
            275                 280                 285

Asp Asn Ala Thr Phe Leu Lys Asn Glu Gln Ala Thr Phe Gln Glu Cys
290                 295                 300

Ala Arg Leu Leu Lys Lys Trp Gly Leu Pro Ala Asn Arg Asn Thr Ile
305                 310                 315                 320

Arg Leu His Asn Glu Phe Thr Ser Thr Ser Cys Pro His Arg Ser Ser
                325                 330                 335

Val Leu His Thr Gly Phe Asp Pro Val Thr Arg Gly Leu Leu Pro Glu
            340                 345                 350

Asp Lys Arg Leu Gln Leu Lys Asp Tyr Phe Ile Lys Gln Ile Arg Ala
        355                 360                 365

Tyr Met Asp Gly Lys Ile Pro Val Ala Thr Val Ser Asn Glu Ser Ser
370                 375                 380

Ala Ser Ser Asn Thr Val Lys Pro Val Ala Glu Leu Met Pro Pro Val
385                 390                 395                 400

Pro Ala Gly Tyr Thr Leu Asp Lys Asn Asn Val Pro Tyr Lys Lys Glu
                405                 410                 415

Gln Gly Asn Tyr Thr Val Ala Asn Val Lys Gly Asn Asn Val Arg Asp
            420                 425                 430

Gly Tyr Ser Thr Asn Ser Arg Ile Thr Gly Val Leu Pro Asn Asn Thr
        435                 440                 445

Thr Ile Thr Tyr Asp Gly Ala Tyr Cys Ile Asn Gly Tyr Arg Trp Ile
450                 455                 460

Thr Tyr Ile Ala Asn Ser Gly Gln Arg Arg Tyr Ile Ala Thr Gly Glu
465                 470                 475                 480

Val Asp Ile Ala Gly Asn Arg Ile Ser Ser Phe Gly Lys Phe Ser Ala
                485                 490                 495

Val

<210> SEQ ID NO 23
<211> LENGTH: 1063
<212> TYPE: PRT
<213> ORGANISM: Artificial Sequence
<220> FEATURE:
<223> OTHER INFORMATION: Synthetic peptide

<400> SEQUENCE: 23

Gln Asn Trp Leu Gly Gly Gly Trp Thr Asp Gly Ile Glu Gln Pro Ala
1               5                   10                  15

Gly Val Gly Lys Lys Leu Gln Asp Asp Asn Met Leu Met Ile Ser Leu
            20                  25                  30

Cys Gly Leu Ser Val Arg Ile Leu Lys Val Arg Gln Arg His Asp Gln
        35                  40                  45

Phe Asn Leu Leu His Lys His Pro Lys Lys Glu Gln Asn Trp Leu Gly
    50                  55                  60

Gly Gly Trp Thr Asp Gly Ile Glu Gln Pro Ala Gly Val Gly Lys Lys
65                  70                  75                  80

Leu Gln Asp Asp Asn Met Leu Met Ile Ser Leu Cys Gly Leu Ser Val
                85                  90                  95

Arg Ile Leu Lys Val Arg Gln Arg His Asp Gln Phe Asn Leu Leu His
            100                 105                 110

Lys His Pro Lys Lys Glu Gln Asn Trp Leu Gly Gly Gly Trp Thr Asp
        115                 120                 125

Arg Ile Glu Gln Pro Gly Trp Gly Trp Glu Lys Val Thr Arg Arg Gln
130                 135                 140
```

```
His Ala Tyr Asp Phe Pro Met Trp Phe Ile Arg Pro Asn Phe Lys Ser
145                 150                 155                 160

Glu Thr Ala Pro Arg Ser Ile Gln Ser Pro Thr Gln Ala Ser Lys Lys
            165                 170                 175

Glu Gln Asn Trp Leu Gly Gly Gly Trp Thr Asp Arg Ile Glu Gln Pro
        180                 185                 190

Gly Trp Gly Trp Glu Lys Val Thr Arg Arg Gln His Ala Tyr Asp Phe
    195                 200                 205

Pro Met Trp Phe Ile Arg Pro Asn Phe Lys Ser Glu Thr Ala Pro Arg
210                 215                 220

Ser Ile Gln Ser Pro Thr Gln Ala Ser Lys Lys Glu Gln Asn Trp Leu
225                 230                 235                 240

Gly Gly Gly Trp Thr Asp Arg Ile Glu Gln Pro Gly Trp Gly Trp Glu
            245                 250                 255

Lys Val Thr Arg Arg Gln His Ala Tyr Asp Phe Pro Met Trp Phe Ile
        260                 265                 270

Arg Pro Asn Phe Lys Ser Glu Thr Ala Pro Arg Ser Ile Gln Ser Pro
    275                 280                 285

Thr Gln Ala Ser Lys Lys Glu Gln Asn Trp Leu Gly Gly Gly Trp Thr
290                 295                 300

Asp Arg Ile Glu Gln Pro Gly Trp Gly Trp Glu Lys Val Thr Arg Arg
305                 310                 315                 320

Gln His Ala Tyr Asp Phe Pro Met Trp Phe Ile Arg Pro Asn Phe Lys
            325                 330                 335

Ser Glu Thr Ala Pro Arg Ser Ile Gln Ser Pro Thr Gln Ala Ser Lys
        340                 345                 350

Lys Glu Gln Asn Trp Leu Gly Gly Gly Trp Thr Asp Gly Ile Glu Gln
    355                 360                 365

Pro Gly Trp Gly Trp Glu Lys Val Thr Arg Arg Gln His Ala Tyr Asp
370                 375                 380

Phe Pro Met Trp Phe Ile Arg Pro Asn Phe Lys Ser Glu Thr Ala Pro
385                 390                 395                 400

Arg Ser Val Gln Ser Pro Thr Gln Ala Pro Lys Lys Glu Gln Asn Trp
            405                 410                 415

Leu Gly Gly Gly Trp Thr Asp Gly Ile Glu Gln Pro Gly Trp Gly Trp
        420                 425                 430

Glu Lys Val Thr Arg Arg Gln His Ala Tyr Asp Phe Pro Met Trp Phe
    435                 440                 445

Ile Arg Pro Asn Phe Lys Ser Glu Ile Ala Pro Arg Ser Val Gln Ser
450                 455                 460

Pro Thr Gln Ala Pro Lys Lys Glu Gln Asn Trp Leu Gly Gly Gly Trp
465                 470                 475                 480

Thr Asp Gly Ile Glu Gln Pro Gly Trp Gly Trp Glu Lys Val Thr Arg
            485                 490                 495

Arg Gln His Ala Tyr Asp Phe Pro Met Trp Phe Ile Arg Pro Asn Phe
        500                 505                 510

Lys Ser Glu Ile Thr Pro Arg Ser Val Gln Ser Pro Thr Gln Ala Pro
    515                 520                 525

Lys Lys Glu Gln Asn Trp Leu Gly Gly Gly Trp Thr Asp Gly Ile Glu
530                 535                 540

Gln Pro Gly Trp Gly Trp Glu Lys Val Thr Arg Arg Gln His Ala Tyr
545                 550                 555                 560

Asp Phe Pro Met Trp Phe Ile Arg Pro Asn Phe Lys Ser Glu Thr Ala
            565                 570                 575
```

-continued

```
Pro Arg Ser Val Gln Ser Pro Thr Gln Ala Pro Lys Glu Gln Asn
            580                 585                 590

Trp Leu Gly Gly Gly Trp Thr Asp Gly Ile Glu Gln Pro Gly Trp Gly
            595                 600                 605

Trp Glu Lys Val Thr Arg Arg Gln His Ala Tyr Asp Phe Pro Met Trp
610                 615                 620

Phe Ile Arg Pro Asn Phe Lys Ser Glu Ile Ala Pro Arg Ser Val Gln
625                 630                 635                 640

Ser Pro Thr Gln Ala Pro Lys Lys Glu Gln Asn Trp Leu Gly Gly Gly
            645                 650                 655

Trp Thr Asp Gly Ile Glu Gln Pro Gly Trp Gly Trp Glu Lys Val Thr
            660                 665                 670

Arg Arg Gln His Ala Tyr Asp Phe Pro Met Trp Phe Ile Arg Pro Asn
            675                 680                 685

Phe Lys Ser Glu Thr Ala Pro Arg Ser Val Gln Ser Pro Thr Gln Ala
            690                 695                 700

Pro Lys Lys Glu Gln Asn Trp Leu Gly Gly Gly Trp Thr Asp Gly Ile
705                 710                 715                 720

Glu Gln Pro Gly Trp Gly Trp Glu Lys Val Thr Arg Arg Gln His Ala
            725                 730                 735

Tyr Asp Phe Pro Met Trp Phe Ile Arg Pro Asn Phe Lys Ser Glu Thr
            740                 745                 750

Ala Pro Arg Ser Val Gln Ser Pro Thr Gln Ala Pro Lys Lys Glu Gln
            755                 760                 765

Asn Trp Leu Gly Gly Gly Trp Thr Asp Gly Ile Glu Gln Pro Gly Trp
770                 775                 780

Gly Trp Glu Lys Val Thr Arg Arg Gln His Ala Tyr Asp Phe Pro Met
785                 790                 795                 800

Trp Phe Ile Arg Pro Asn Phe Lys Ser Glu Thr Ala Pro Arg Ser Val
            805                 810                 815

Gln Ser Pro Thr Gln Ala Pro Lys Lys Glu Gln Asn Trp Leu Gly Gly
            820                 825                 830

Gly Trp Thr Asp Gly Ile Glu Gln Pro Gly Trp Gly Trp Glu Lys Val
            835                 840                 845

Thr Arg Arg Gln His Ala Tyr Asp Phe Pro Met Trp Phe Ile Arg Pro
850                 855                 860

Asn Phe Lys Ser Glu Thr Ala Pro Arg Ser Val Gln Ser Pro Thr Gln
865                 870                 875                 880

Ala Pro Lys Lys Glu Gln Asn Trp Leu Gly Gly Gly Trp Thr Asp Gly
            885                 890                 895

Val Gln Gln Pro Gly Ser Gly Trp Glu Lys Val Thr Arg Arg Gln His
            900                 905                 910

Ala Tyr Asp Phe Pro Met Trp Phe Ile Arg Pro Asn Phe Lys Ser Glu
            915                 920                 925

Thr Ala Pro Arg Ser Val Gln Ser Pro Thr Gln Ala Ser Lys Lys Glu
            930                 935                 940

Gln Asn Trp Leu Gly Gly Gly Trp Thr Asp Gly Ile Glu Gln Pro Gly
945                 950                 955                 960

Trp Gly Trp Glu Lys Val Thr Arg Arg Gln His Ala Tyr Asp Phe Pro
            965                 970                 975

Met Phe Phe Ile Arg Pro Lys Phe Lys Thr Ala Thr Ala Thr Arg Ser
            980                 985                 990

Ala Gln Ser Pro Thr Gln Ser Val  Lys Lys Ala Gln Asn  Trp Leu Gly
            995                 1000                1005
```

```
Gly Gly Trp Thr Asn Gly Pro Glu Gln Gly Gly Thr Gly Trp Glu
    1010            1015            1020

Lys Ala Thr Arg Arg Thr His Gly Tyr Asp Phe Pro Met Trp Phe
    1025            1030            1035

Ile Arg Pro Asn Phe Lys Gln Thr Asp Val Thr Val Lys Ser Ser
    1040            1045            1050

Gln Ser Ala Thr Val Gly Asp Lys Lys Ser
    1055            1060

<210> SEQ ID NO 24
<211> LENGTH: 180
<212> TYPE: PRT
<213> ORGANISM: Artificial Sequence
<220> FEATURE:
<223> OTHER INFORMATION: Synthetic peptide

<400> SEQUENCE: 24

Met Lys Ser Gln Gln Gln Ala Lys Asp Trp Ile Tyr Lys His Glu Gly
1               5                   10                  15

Val Gly Val Asp Phe Asp Gly Ala Tyr Gly Phe Gln Cys Met Asp Leu
                20                  25                  30

Ala Val Ala Tyr Ile Tyr Tyr Ile Thr Asp Gly Lys Val Arg Met Trp
            35                  40                  45

Gly Asn Ala Lys Asp Ala Ile Asn Asn Asp Phe Lys Met Lys Ser Gln
        50                  55                  60

Gln Gln Ala Lys Glu Trp Ile Tyr Lys His Glu Gly Ala Gly Val Asp
65                  70                  75                  80

Phe Asp Gly Ala Tyr Gly Phe Gln Cys Met Asp Leu Ser Val Ala Tyr
                85                  90                  95

Val Tyr Tyr Ile Thr Asp Gly Lys Val Arg Met Trp Gly Asn Ala Lys
                100                 105                 110

Asp Ala Ile Asn Asn Asp Phe Lys Met Lys Ser Gln Gln Gln Ala Lys
            115                 120                 125

Glu Trp Ile Tyr Asn His Glu Gly Ala Gly Val Asp Phe Asp Gly Ala
        130                 135                 140

Tyr Gly Phe Gln Cys Met Asp Leu Ala Val Ala Tyr Val Tyr Tyr Ile
145                 150                 155                 160

Thr Asp Gly Lys Val Arg Met Trp Gly Asn Ala Lys Asp Ala Ile Asn
                165                 170                 175

Asn Asp Phe Lys
            180
```